US007960526B2

(12) United States Patent
Hodges et al.

(10) Patent No.: US 7,960,526 B2
(45) Date of Patent: Jun. 14, 2011

(54) COLORIMETRIC-OXYCARBONYL PROTECTING GROUPS FOR USE IN ORGANIC SYNTHESES

(75) Inventors: John C. Hodges, Ann Arbor, MI (US); Yam Foo Poon, Ann Arbor, MI (US); William H. Pearson, Chicago, IL (US)

(73) Assignee: Berry and Associates, Inc., Dexter, MI (US)

( * ) Notice: Subject to any disclaimer, the term of this patent is extended or adjusted under 35 U.S.C. 154(b) by 305 days.

(21) Appl. No.: 12/414,288

(22) Filed: Mar. 30, 2009

(65) Prior Publication Data

US 2010/0249393 A1   Sep. 30, 2010

(51) Int. Cl.
*C07H 21/02* (2006.01)
*C07H 21/04* (2006.01)

(52) U.S. Cl. ............ 536/23.1; 536/22.1; 536/24.3; 536/25.3; 536/26.1; 536/27.1; 536/27.13

(58) Field of Classification Search .................. None
See application file for complete search history.

(56) References Cited

U.S. PATENT DOCUMENTS

| 4,725,677 | A | 2/1988 | Koster et al. |
| 5,235,091 | A | 8/1993 | Kato et al. |
| 5,869,579 | A | 2/1999 | Hodges et al. |
| 5,922,890 | A | 7/1999 | Bleicher |
| 5,932,696 | A | 8/1999 | Hodges et al. |
| 6,239,220 | B1 | 5/2001 | Sanghvi et al. |
| 6,828,435 | B2 | 12/2004 | Koster et al. |
| 2009/0029866 | A1 | 1/2009 | Southern et al. |

OTHER PUBLICATIONS

Kwang-Seuk Ko et al., "Protecting-Group-Based Colorimetric Monitoring of Fluorous-Phase and Solid-Phase Synthesis of Oligoglucosamines,", Organic Letters 2008, vol. 10, No. 23., pp. 5381-5384; Published on Web on Nov. 1, 2008.
Eckart Leikauf et al., "A New Colorimetric Protecting Group Allowing Deprotection Under Neutral Conditions", Tetrahedron vol. 51, No. 19, pp. 5557-5562; Mar. 1995.
Robert Ramage et al., Comparative Studies of Nsc and Fmoc as N-protecting Groups for SPPS; Journal of Peptide Science 5: pp. 195-200; Feb. 1999.
Andres S. Hernandez et al., "Solid-Supported tert-Alkoxycarbonylation Reagents for Anchoring of Amines during Solid Phase Organic Synthesis"; Journal of Organic Chemistry; 1997, 62, pp. 3153-3157; Jan. 1997.
Catalog "Specialty Reagents for Oligonucleotide Synthesis and Purification"; Berry & Associates; Jan. 2006; pp. 1-72.
The Glen Report, vol. 19, No. 1, Apr. 2007, pp. 1-16.
International Search Report—PCT/US2010/028656 (Mar. 25, 2010).

*Primary Examiner* — Patrick Lewis
(74) *Attorney, Agent, or Firm* — Brinks Hofer Gilson & Lione

(57) ABSTRACT

The present invention provides for reagents for the introduction of colorimetric-oxycarbonyl protecting groups, compounds bearing colorimetric-oxycarbonyl protecting groups, and the use thereof in solid-supported organic syntheses of oligonucleotides, polypeptides, polysaccharides, and combinatorial libraries.

20 Claims, No Drawings

COLORIMETRIC-OXYCARBONYL PROTECTING GROUPS FOR USE IN ORGANIC SYNTHESES

FIELD OF THE INVENTION

This invention pertains to acid-labile protecting groups that are used to protect heteroatoms during solid-supported organic syntheses. In particular, the invention pertains to heteroatom protecting groups that generate a detectable color when cleaved from a reaction product. These protecting groups are herein referred to as "Colorimetric-oxycarbonyl protecting groups" or "Cmoc protecting groups" for short. The color generated by the cleavage of a Cmoc protecting group is particularly useful in the automation of solid-supported organic syntheses since it provides a convenient and quantitative means of measuring the progress of key synthesis steps.

BACKGROUND

Frequently, it is desirable to mask or protect the reactivity of heteroatoms during the course of multi-step organic syntheses. A textbook that summarizes the utility of a wide variety of heteroatom protecting groups has been published by Peter G. M. Wuts and Theodora W. Greene (*Greene's Protective Groups in Organic Synthesis*, Wiley, 2006). Oxycarbonyl protecting groups such as Cbz, Boc, Fmoc, and the like are known to in the art. For example, N-Boc or N-Fmoc protection strategies are used in automated solid-phase peptide synthesizers that are currently available. Similarly, tri-arylmethyl protecting groups such as DMT, MMT, Tr, and the like are known to those skilled in the art. For example, the O-DMT protection strategy is used in automated oligonucleotide synthesizers that are currently available.

Colorimetric analysis of synthetic intermediates during the course of multi-step syntheses on solid supports such as peptide synthesis, oligonucleotide synthesis, polysaccharide synthesis, and combinatorial chemistry is a valuable means for assessing the result of key synthetic steps. For example, in automated, solid-supported peptide synthesis, monitoring the characteristic absorbance of 1-((9H-fluoren-9-yl)methyl)piperidine during the cleavage of an Fmoc protecting group from the amino terminus of the growing peptide provides valuable information as to the progress of the synthesis. Similarly in automated, solid-supported oligonucleotide synthesis monitoring the absorbance of light at a wavelength of about 498 nM, which is indicative of the DMT-cation that is produced during the cleavage of a DMT protecting group from the 5'-hydroxyl terminus of the growing oligonucleotide, provides valuable information as to the progress of the synthesis. Similarly in automated, solid-supported polysaccharide synthesis and combinatorial chemistry the calorimetric monitoring of the presence of primary amino groups with a ninhydrin test provides valuable information as to the progress of the synthesis.

The 2-(4-nitrophenyl)sulfonylethoxycarbonyl protecting group, which provides an enhanced calorimetric signal upon basic cleavage as compared to the Fmoc protecting group, has been described by Ramage et al. (*Journal of Peptide Science*, 5(4), 199-200, 1999). The preparation and characterization of a homologous series of solid phase synthesis resins for anchoring amines via a Boc-like linker has been described by Hernandez et al. (*Journal of Organic Chemistry*, 62(10), 3153-7, 1997). The 4-(4-nitrophthalimido)butyrate protecting group for alcohols, which provides a calorimetric signal upon cleavage with hydrazine acetate has been described by Ko et al. (*Organic Letters*, 10(23), 5381-4, 2008). The protection of alcohols by treatment with the symmetrical anhydride of 5-(3-(hydroxybis(4-methoxyphenyl)methyl)phenoxy)-4-oxopentanoic acid and the subsequent deprotection with a hydrazine-pyridinium acetate buffer at nearly neutral pH to provide a calorimetric signal have been described by Leikauf et al. (*Tetrahedron*, 51(19), 5557-62, 1995).

SUMMARY OF THE INVENTION

In one aspect, the present invention provides for compounds of Formula I

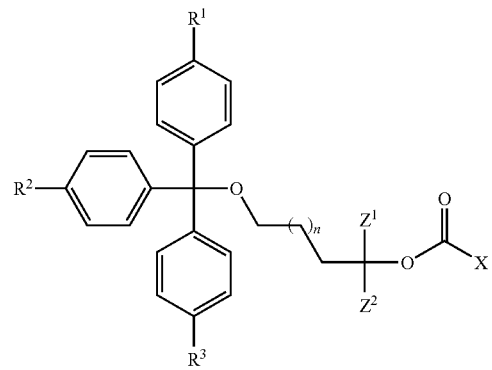

wherein:
$R^1$, $R^2$, and $R^3$ are each independently H, Br, Cl, F, R, or OR, wherein R is $C_1$-$C_6$-alkyl;
X is selected from the group consisting of an acyl-leaving group, a
  $C_1$-$C_6$-alkyl ester of an amino acid, an active ester of an amino acid, an amino acid, an amino alcohol, an amino ether, an amino alcohol-O-phosphoramidite, an amino-nucleoside, an amino-nucleoside-O-phosphoramidite, and a diamine;
n is an integer that is selected from 0 to 8;
$Z^1$ and $Z^2$ are each independently $C_1$-$C_6$-alkyl, or aryl;
or a salt thereof. In certain embodiments, $R^1$, $R^2$, and $R^3$ are each independently H, Cl, or $CH_3O$, and $Z^1$ and $Z^2$ are identical. In other embodiments, $R^1$ is H, $R^2$ and $R^3$ are both $CH_3O$, and $Z^1$ and $Z^2$ are identical. In other embodiments, $Z^1$ and $Z^2$ are $CH_3$, Ph, or 4-Cl-Ph. In other embodiments, X is an acyl-leaving group. In certain embodiments, X is a $C_1$-$C_6$-alkyl ester of an amino-acid. In still other embodiments, X is an active ester of an amino-acid. In particular embodiments, X is an amino-acid. In yet other embodiments, X is an amino-alcohol. In certain embodiments, X is an amino-ether. In other embodiments, X is an amino-alcohol-O-phosphoramidite. In certain embodiments, X is an amino-nucleoside. In certain embodiments, X is an amino-nucleoside-O-phosphoramidite. In certain embodiments, X is a diamine. In certain embodiments, $R^1$ is H, $R^2$ and $R^3$ are $OCH_3$, X is 1-imidazolyl, n is 1, and $Z^1$ and $Z^2$ are selected from the group consisting of $CH_3$, Ph, or 4-Cl-Ph.

When X is a $C_1$-$C_6$-alkyl ester of an amino acid, an active ester of an amino acid, an amino acid, an amino alcohol, an amino ether, an amino alcohol-O-phosphoramidite, an amino-nucleoside, an amino-nucleoside-O-phosphoramidite, or a diamine, it is bonded through an amino group on that group to the oxycarbonyl group (—O(C=O)—) of the rest of the compound. For example, if X is the amino-nucleoside 5'-amino-2'-5-dideoxyinosine, then the compound could be represented as follows:

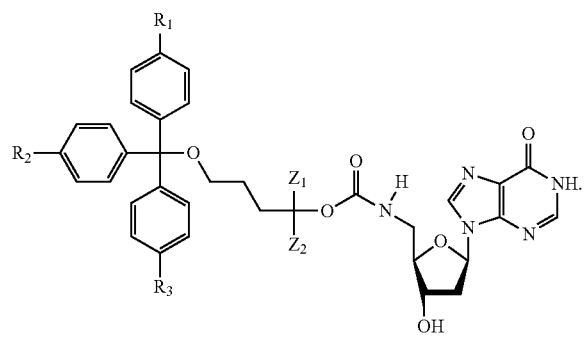

Another example would be if X is the amino alcohol $NH_2(CH_2)_3OCH_2CH_2OH$, then resulting compound could be represented as follows:

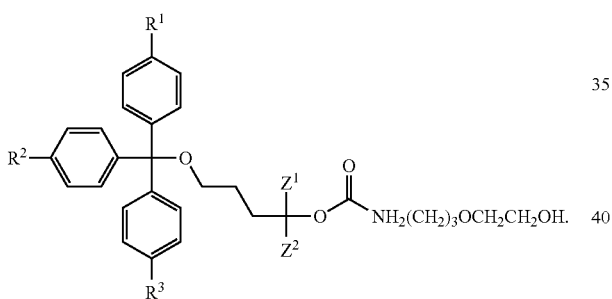

In certain embodiments, the present invention relates to compounds of formula II wherein R is H or Cl:

In certain embodiments, the present invention relates to compounds of formula III:

III

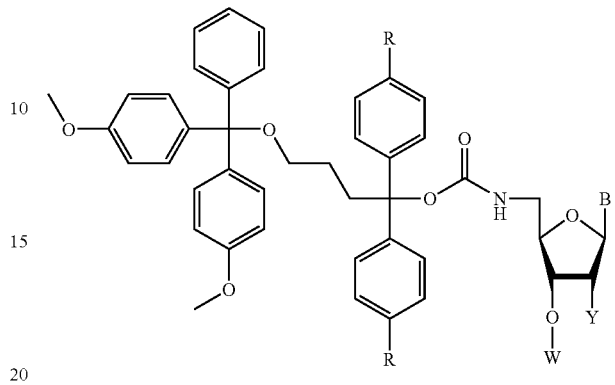

wherein: R is H or Cl;

B is selected from the group consisting of:

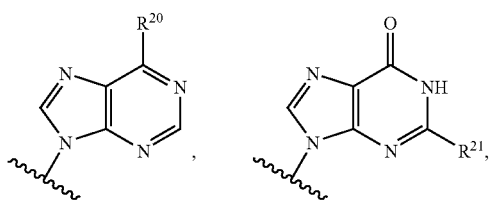

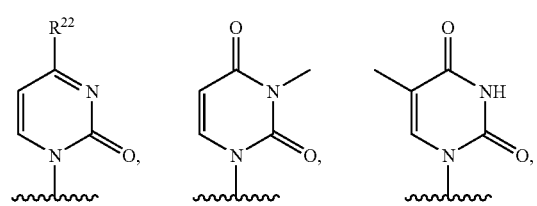

II

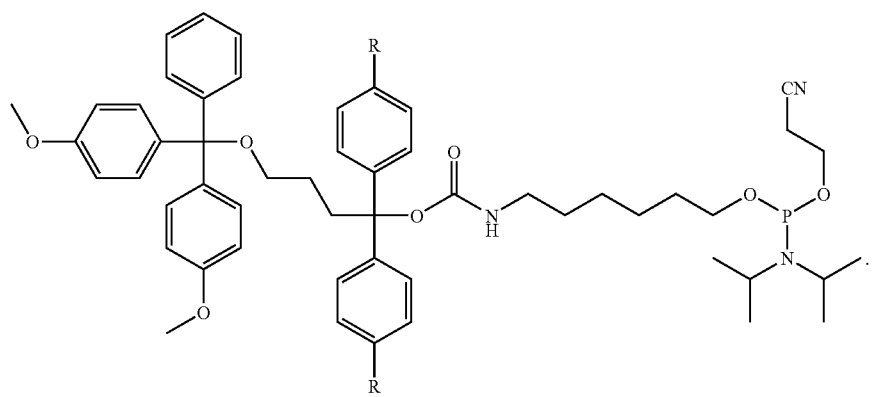

-continued

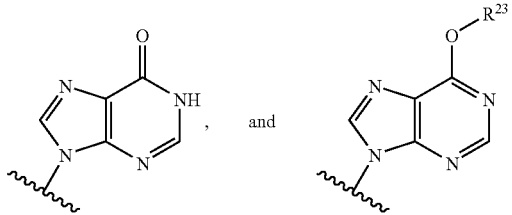

$R^{20}$ is selected from the group consisting of: $NH_2$, $NHC(O)Ph$, $NHC(O)CH_3$, $NH(C_1\text{-}C_6\text{-alkyl})$, and $N=CHN(C_1\text{-}C_6\text{-alkyl})_2$;

$R^{21}$ is selected from the group consisting of: $NH_2$, $NHC(O)CH(CH_3)_2$, $NHC(O)N(Ph)_2$, and $N=CHN(C_1\text{-}C_6\text{-alkyl})_2$;

$R^{22}$ is selected from the group consisting of: $NH_2$, $NHC(O)Ph$, $NHC(O)CH_3$, and $N=CHN(C_1\text{-}C_6\text{-alkyl})_2$;

$R^{23}$ is selected from the group consisting of: H, phenyl, 4-chlorophenyl, (4-nitrophenyl)ethyl, and 2-cyanoethyl;

Y is H, OH, $OCH_3$, $-OSi(t\text{-}Bu)Me_2$, $-OCH_2OSi(i\text{-}Pr)_3$, or $-OCH(OCH_2CH_2OAC)_2$; and W is H or $-OP(OCH_2CH_2CN)N(i\text{-}Pr)_2$.

In certain embodiments, the present invention relates to compounds of formula IV:

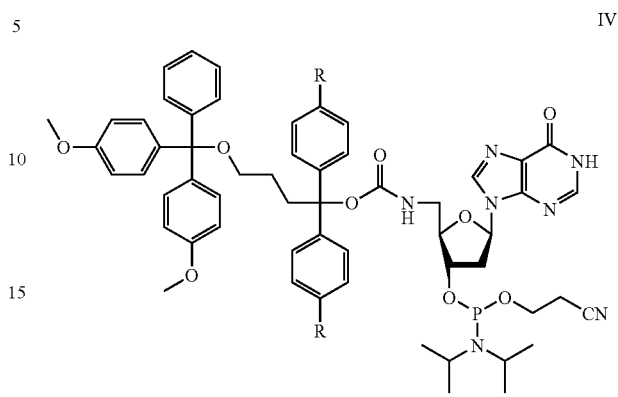

IV wherein R is H or Cl.

In certain embodiments, the present invention relates to compounds selected from the group consisting of:

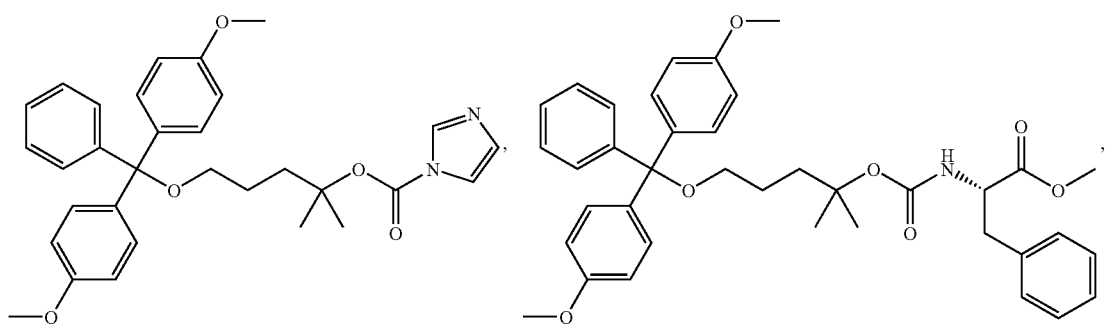

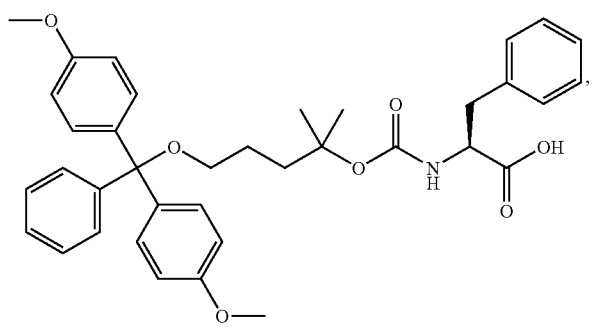

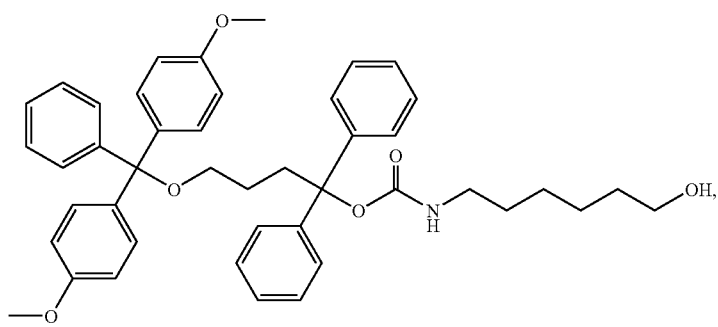

-continued
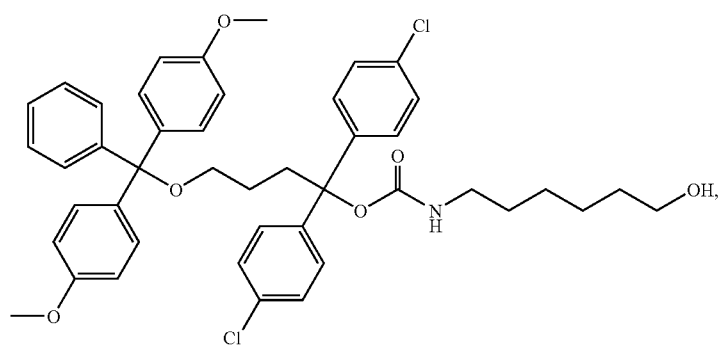
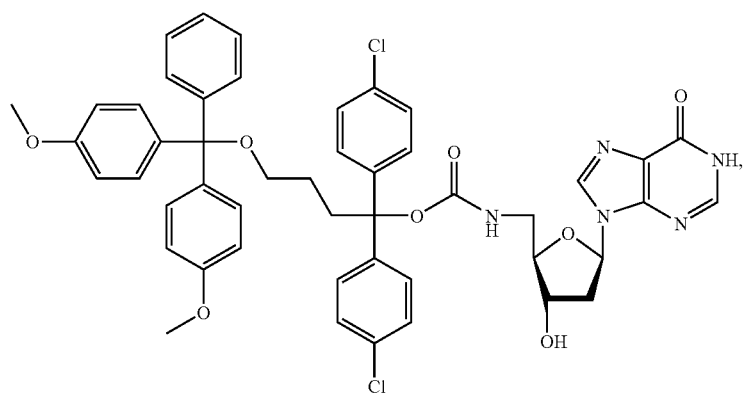
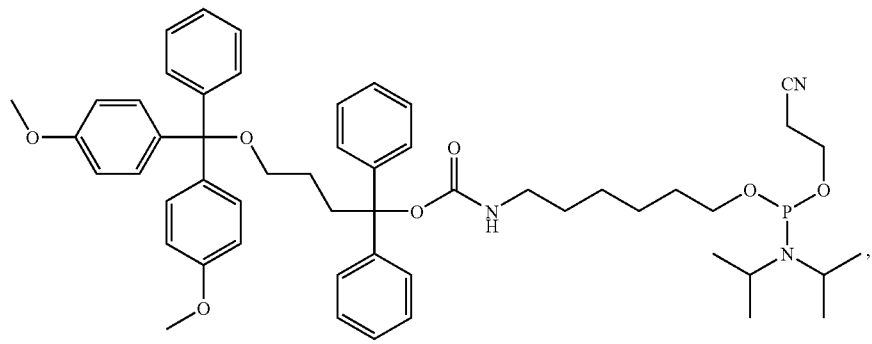
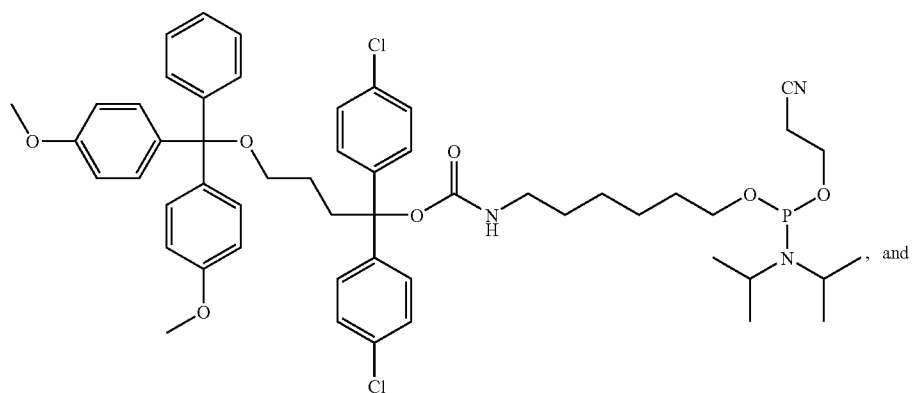

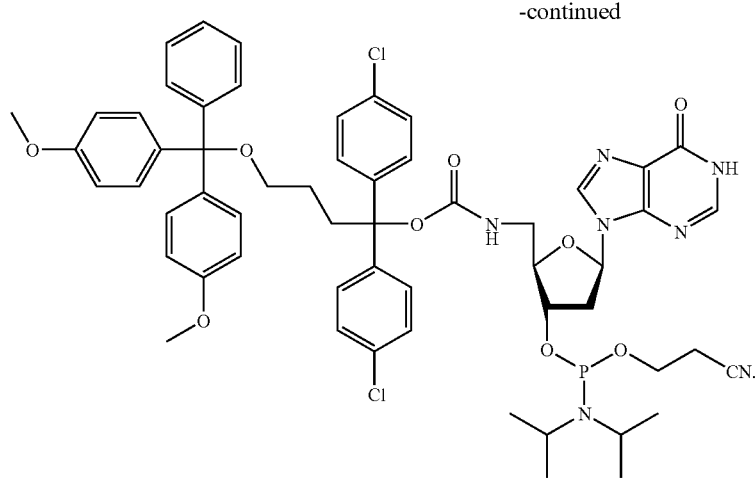

In another aspect, the present invention relates to compounds of formula V:

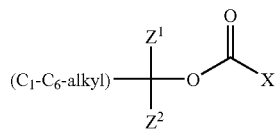

wherein
Z$^1$ and Z$^2$ are each independently aryl; and
X is selected from the group consisting of an acyl-leaving group,
a C$_1$-C$_6$-alkyl ester of an amino acid, an active ester of an amino acid, an amino acid, an amino alcohol, an amino ether, an amino alcohol-O-phosphoramidite, an amino-nucleoside, an amino-nucleoside-O-phosphoramidite, or a diamine;
or a salt thereof. Compounds of formula V typically do not generate a calorimetric signal upon cleavage from a reaction product and are thus useful as negative controls for a compound of formula I.

DEFINITIONS

1. "Active ester" means an ester that is readily converted to an amide when reacted with a primary or secondary amine. Examples of active esters that are known to one skilled in the art of organic chemistry include but are not limited to pentafluorophenyl ester, 4-nitrophenyl ester, phenyl ester, N(1)-hydroxysuccinimide ester, N(1)-hydroxyphthalimide ester, N(1)-hydroxybenzotriazole ester, N(1)-hydroxy-7-azo-benzotriazole ester, 1,1,1,3,3,3-hexafluoro-2-propyl ester, 2-(N-hydroxyimino)-2-phenylacetonitrile ester, and the like.

2. "Acyl-leaving group" means an atom or group of atoms that is displaced from the carbon atom of a carbonyl group by an amine, an alcohol, or a thiol in a reaction that forms an amide, a urea, an ester, a carbamate, a thioester, a carbonate, a thiocarbamate, or a thiocarbonate group. Examples of acyl-leaving groups that are known to one skilled in the art of organic chemistry include but are not limited to fluoride, chloride, imidazole, N-methylimidazolium triflate, triazole, 4-nitrophenol, pentafluorophenol, pentachlorophenol, 1,1,1,3,3,3-hexafluoro-2-propanol, N-hydroxysuccinimide, N-hydroxyphthalimide, 1-hydroxybenzotriazole, 7-aza-1-hydroxybenzotriazole, 2-(N-hydroxyimino)-2-phenylacetonitrile, and the like.

3. "Amino-acid" means an alpha-amino-acid, a beta-amino-acid, or an omega-amino-acid with a molecular weight less than 1,000 atomic mass units, including any carboxyl, amino, thiol, and hydroxyl protecting groups attached thereto. The following are examples of protecting groups on amino acids. The carboxyl groups of amino-acids may be protected as their C$_1$-C$_6$-alkyl esters or as their benzyl esters. The amino groups of amino-acids may be protected by groups such as Boc, Cbz, Fmoc, and Tr. The thiol groups of amino-acids such as Cys may be protected with groups such as 2-cyanoethyl, t-butyl, benzyhydryl, Tr, MMT, and DMT. The hydroxyl groups of amino acids such as Ser, Thr, and Tyr may be protected with groups such as 2-cyanoethyl, acetyl, pivaloyl, benzoyl, toluoyl, t-butyl, benzyl, 4-methoxybenzyl, benzyhydryl, Tr, t-butyldimethylsilyl, tri-isopropylsilyl, t-butyldiphenylsilyl, and tetrahydropyran-1-yl. Examples of alpha-amino-acids include, but are not limited to, D and L versions of Ala, Cys, Asp, Glu, Phe, Gly, His, Ile, Lys, Orn, Leu, Met, Asn, Pro, Gln, Arg, Ser, Thr, Val, Trp, and Tyr. Examples of beta-amino-acids and omega-amino-acids include, but are not limited, to 3-aminopropanoic acid, 4-aminobutanoic acid, 5-aminopentanoic acid, 6-aminohexanoic acid, and 7-aminoheptanoic acid.

4. "Amino-alcohol" means a straight chain, branched chain, or cyclic hydrocarbon that contains at least two (2) but not more than twelve (12) carbon atoms, at least one primary or secondary amino group, and at least one hydroxyl group. Examples of amino alcohols include compounds of the formula NH$_2$—(C$_2$-C$_{12}$ straight or branched chain alkyl)-OH, compounds of the formula of NH$_2$—(C$_3$-C$_7$ cycloalkyl)-OH, compounds of the formula (aza-(C$_3$-C$_6$-cycloalkyl))-CH$_2$OH, compounds of the formula (aza-(C$_3$-C$_6$-cycloalkyl))-CH$_2$CH$_2$OH, and N-(hydroxy-(C$_2$-C$_8$-straight or branched chain alkyl))-piperazine. Examples of amino alcohols include, but are not limited to, 4-amino-cyclohexanol, 3-amino-cyclohexanol, 2-aminocyclohexanol, 3-hydroxypiperidine, 4-hydroxypiperidine, 4-hydroxymethyl-piperidine, 3-hydroxymethyl-piperidine, 2-hydroxymethyl-piperidine, 3-hydroxymethyl-pyrrolidine, 2-hydroxymethyl-pyrrolidine, 3-hydroxy-pyrrolidine, N-(2-hydroxyethyl)-piperazine, N-(3-hydroxypropyl)-piperazine, 12-amino-dodecan-1-ol, 11-amino-undecan-1-ol, 10-amino-decan-1-ol, 9-amino-nonan-1-ol, 8-amino-octan-1-ol, 7-amino-heptan- 1-ol, 6-amino-hexan-1-ol 5-amino-pentan-1-ol, 4-amino-butan-1-ol, 2-amino-propan-1-ol, 3-amino-propan-1-ol, 1-amino-propan-2-ol, 2-amino-2-methyl-propan-1-ol, 3-amino-2-hydroxy-propan-1-ol, and 2-amino-ethanol.

5. "Amino-ether" means an a straight chain, branched chain, or cyclic hydrocarbon that contains not more than fifteen (15) carbon atoms, at least one primary or secondary amino group, and at least one ether group included within the hydrocarbon. Amino-ethers may also contain hydroxyl groups and/or hydroxyl groups that are protected by groups that may be removed under non-acidic conditions (the carbon atoms of protecting groups are not counted in the limit of fifteen (15) carbon atoms above). Examples of amino-ethers include, but are not limited to, compounds of the formula $NH_2(CH_2)_p(OCH_2CH_2)_qOR$, compounds of the formula $NH_2(CH_2)_p(OCH_2CH_2)_qO(CH_2)_pNH_2$, compounds of the formula $NH_2(CH_2)_p(OCH_2CH_2)_qOCH_2(OH)CH_2OR$, compounds of the formula $RO(CH_2)_pNH(CH_2)_qOR$, and compounds of the formula $NH_2(CH_2)_pCH[(CH_2)_qOR]_2$ wherein p and q are integers that limit the formulae to but not more than fifteen (15) carbon atoms and R is independently H or a hydroxyl protecting group. Examples of hydroxyl protecting groups that are known to those skilled in the art of organic chemistry include, but are not limited, to acetyl, pivaloyl, benzoyl, toluoyl, benzyl, benzhydryl, 4-methoxybenzyl, tetrahydropyran-2-yl, t-butyl(dimethyl)silyl, triethylsilyl, tri(isopropyl)silyl, 2-(trimethylsilyloxy)ethyl, and 2,2,2-trichloroethyl. Examples of amino ethers include, but are not limited to, $NH_2(CH_2)_3OCH_2CH_2OH$, $NH_2(CH_2)_2(OCH_2CH_2)_3OH$, $NH_2(CH_2)_3(OCH_2CH_2)_4OH$, $NH_2(CH_2)_2(OCH_2CH_2)_3O(CH_2)_2NH_2$, $NH_2(CH_2)_3(OCH_2CH_2)_3O(CH_2)_3NH_2$, $NH_2(CH_2)_2(OCH_2CH_2)_4O(CH_2)_2NH_2$, $NH_2(CH_2)_3(OCH_2CH_2)_4O(CH_2)_3NH_2$, $NH_2(CH_2)_3OCH_2(OH)CH_2OH$, $NH_2(CH_2)_3OCH_2(OH)CH_2OPiv$, $NH_2(CH_2)_3OCH_2CH_2OCH_2(OH)CH_2OSi(Et)_3$, $NH_2(CH_2)_3(OCH_2CH_2)_3OCH_2(OH)CH_2OSi(CH_3)_2t$-Bu, $HO(CH_2)_nNH(CH_2)_mOH$, $HO(CH_2)_2NH(CH_2)_3OSi(Et)_3$, $HO(CH_2)_2NH(CH_2)_3OSi(CH_3)_2t$-Bu, $NH_2CH_2CH[(CH_2)_2OH]_2$, and $NH_2CH_2CH[(CH_2)_2OH][(CH_2)_2OSi(CH_3)_2t$-Bu].

6. "Amino-nucleoside" means a nucleoside wherein one of the hydroxyl groups of the ribose or 2'-deoxyribose is replaced by an amino group. Examples of an amino-nucleoside include, but are not limited to, compounds of formula VI and of formula VII:

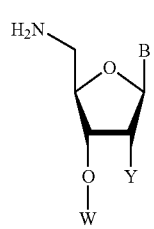

VI

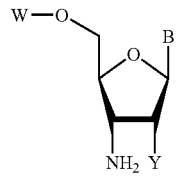

VII wherein:
R is H or Cl;
B is selected from the group consisting of:

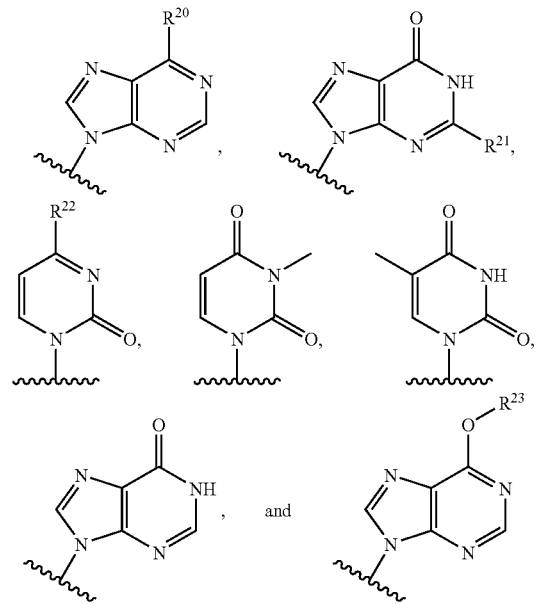

$R^{20}$ is selected from the group consisting of: $NH_2$, $NHC(O)Ph$, $NHC(O)CH_3$, $NH(C_1$-$C_6$-alkyl), and $N=CHN(C_1$-$C_6$-alkyl)$_2$;

$R^{21}$ is selected from the group consisting of: $NH_2$, $NHC(O)CH(CH_3)_2$, $NHC(O)N(Ph)_2$, and $N=CHN(C_1$-$C_6$-alkyl)$_2$;

$R^{22}$ is selected from the group consisting of: $NH_2$, $NHC(O)Ph$, $NHC(O)CH_3$, and $N=CHN(C_1$-$C_6$-alkyl)$_2$;

$R^{23}$ is selected from the group consisting of: H, phenyl, 4-chlorophenyl, (4-nitrophenyl)ethyl, and 2-cyanoethyl;

Y is H, OH, $OCH_3$, $-OSi(t$-Bu)Me$_2$, $-OCH_2OSi(i$-Pr)$_3$, or
$-OCH(OCH_2CH_2OAc)_2$; and
W is H or $-OP(OCH_2CH_2CN)N(i$-Pr)$_2$.

7. "Aryl" means an unsubstituted phenyl ring, or a phenyl ring that is substituted with one to five substituents independently selected from the group consisting of: F, Cl, Br, I, OR, OPh, $CF_3$, $CCl_3$, or $C_1$-$C_6$-alkyl, where R is a $C_1$-$C_6$-alkyl.

8. "$C_1$-$C_6$-alkyl" means a monovalent radical of a straight or branched alkane having from one to six carbons. Examples of $C_1$-$C_6$ straight-chain alkyl groups include methyl, ethyl, n-propyl, n-butyl, n-pentyl, and n-hexyl. Examples of branched-chain alkyl groups include, but are not limited to, isopropyl, tert-butyl, isobutyl, isoamyl, neopentyl, etc.

9. "$C_3$-$C_7$-cycloalkyl" means a monovalent radical of a cyclic alkane having from three to seven carbons. Examples of "$C_3$-$C_7$-cycloalkyls" include, but are not limited to, cyclopropyl, cyclobutyl, cyclopentyl, cyclohexyl, cycloheptyl, cyclopropylmethyl, 1-methylcyclopropyl, 2-methylcyclopropyl, 1-cyclopropyl-ethyl, 2-cyclopropyl-ethyl, 1-cyclopropyl-propyl, 2-cyclopropyl-propyl, 3-cyclopropyl-propyl, cyclobutylmethyl, 1-cyclobutyl-ethyl, 2-cyclobutyl-ethyl, 2-methylcyclopentyl, cyclopentylmethyl, cyclopentylethyl, 2-methylcyclohexyl, and cyclohexylmethyl.

10. "Combinatorial chemistry" refers to concurrently synthesizing a set of many analogous compounds, called a combinatorial library, from at least two groups of similar reagents by allowing various combinations of a reagent of the first group to react with a reagent of the second group. Combinatorial chemistry may be carried out either in solution or on solid support and may be organized for greater synthetic efficiency by and either by parallel or mixture paradigms that are known to those skilled in the art of combinatorial chemistry. Frequently, combinatorial chemistry employs automated synthesis equipment.

11. "Diamine" means a $C_2$-$C_{12}$ straight or branched chain alkyl group containing at least two amino groups wherein the amino group may be a primary or secondary amino group; a $C_3$-$C_7$ cycloalkyl substituted with at least two amino groups, wherein the amino group may be a primary or secondary amino group; or a $C_3$-$C_7$ nitrogen containing cycloalkyl group (e.g., piperazine) containing two secondary amino groups in the ring, or one secondary amino group in the ring (e.g., aziridine, azetidine, pyrrolidine, piperidine, and azepine), and is substituted with a primary or secondary amino group or a $C_1$-$C_6$ alkyl that is substituted with a primary or secondary amino group. Examples of diamines include, but are not limited to, piperazine, 4-aminopiperidine, 4-aminomethyl-piperidine, 3-aminomethyl-piperidine, 1-(2-aminoethyl)piperazine, 1,6-diaminohexane, 1,4-diaminobutane, 1,3-diamino-propane, ethylenediamine, N-methyl-ethylenediamine, and 6-methylamino-hexylamine.

12. "Heteroatom" means a nitrogen atom, an oxygen atom, or a sulfur atom.

13. "Nucleoside" means the repeating synthon of RNA or DNA that is composed of a heterocyclic base and a ribose or a 2'-deoxyribose. As used in this disclosure, nucleoside refers to both natural and unnatural nucleosides that are known by those skilled in the art to be useful to oligonucleotide synthesis. Examples of natural nucleosides include uridine, cytosine, adenosine, guanosine, inosine, thymidine, 2'-deoxyuridine, 2'-deoxycytosine, 2'-deoxyadenosine, 2'-deoxyguanosine and 2'-deoxyinosine. Examples of unnatural nucleosides include, but are not limited to, those analogs of natural nucleosides with one or more of the following five types of modifications to the heterocyclic base: (1) A ring nitrogen atom of the heterocyclic base has been replaced by a carbon atom; (2) A ring carbon atom of the heterocyclic base has been replaced by a nitrogen atom; (3) An oxygen atom or hydroxyl group of the heterocyclic base has been replaced by a hydrogen atom, a chlorine atom, a fluorine atom, a sulfur atom or thiol group, an amino group, a nitro ($NO_2$) group, or a $C_1$-$C_6$-alkyl group; (4) An amino group of the heterocyclic base has been replaced by a hydrogen atom, a chlorine atom, a fluorine atom, a hydroxyl group, a thiol group, or, a nitro ($NO_2$) group, or a $C_1$-$C_6$-alkyl group; and (5) A hydrogen atom of the heterocyclic base has been replaced by an amino group, a hydroxyl group, a thiol group, a nitro ($NO_2$) group, or a $C_1$-$C_6$-alkyl group.

14. "Nucleoside phosphoramidite" means a synthon of RNA or DNA that is a nucleoside wherein all but one of the hydroxyl groups on the ribose or deoxyribose are suitably protected and the remaining hydroxyl group is activated as a phosphoramidite, rendering the nucleoside useful for oligonucleotide synthesis. For example, in a typical nucleoside phosphoramidite the 5'-hydroxyl group is suitably protected by DMT, the 3' hydroxyl group is activated as an N,N-diisopropylamino, 2-cyanoethoxy-phosphoramidite, and if there is a 2'-hydroxyl group present, it is suitably protected by one of the following groups: —$CH_3$, —$Si(t\text{-}Bu)Me_2$, —$Si(t\text{-}Bu)Ph_2$, —$CH_2OSi(i\text{-}Pr)_3$, or —$CH(OCH_2CH_2OAc)_2$.

15. "Nucleotide" means a synthon of RNA or DNA that is composed of a heterocyclic base, a ribose or a deoxyribose, and a phosphate. As used in this disclosure, nucleotide refers to both natural and unnatural nucleotides that are known by those skilled in the art to be useful to oligonucleotide science.

16. "Modifier" means a synthon that adds a functional group with useful reactivity, such as for example an amino group, a thiol group or a carboxyl group, to an oligonucleotide, peptide, or polysaccharide. Typically a modifier is attached with the useful functional group in protected form then the protecting group is removed when the reactivity of the useful functional group is required.

17. "Oligonucleotide" means a segment of single stranded DNA or RNA, typically fewer than 100 nucleotides in length. As used in this disclosure, oligonucleotides may be composed of both natural and unnatural nucleotides and may contain other modifiers and tags that are known in the art to be useful in oligonucleotide synthesis.

18. "Peptide" and "polypeptide" are interchangeable terms that mean a linear chain of alpha-amino-acids (typically 2 to 50) that are linked in head to tail fashion by amide bonds, also known as peptide bonds. As used in this disclosure, peptides may be composed of both natural and unnatural amino-acid units and may contain other modifiers and tags that are known by those skilled in the art to be useful to peptide science.

19. "Phosgene Equivalent" means a reagent that allows for acylation on both sides of a carbonyl moiety (CO). Phosgene is Cl—C(O)—Cl. Examples of phosgene equivalents include, but are not limited to, triphosgene and compounds of the formula X—C(O)—X wherein X is selected from imidazol-1-yl, 3-methyl-imidazol-1-yl triflate, phenoxy, (2,3,4,5,6-pentafluorophenyl)oxy, (4-nitrophenyl)oxy, N(1)-oxysuccinimide, N(1)-oxyphthalimide, N(1)-oxy-benzotriazole, and 7-aza-N(1)-oxy-benzotriazole.

20. "Phosphoramidite" means a phosphityl moiety with two ester and one amide linkages. An example of phosphoramidite is a moiety of the following structure:

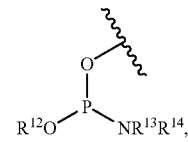

where $R^{12}$ is methyl, benzyl, or cyanoethoxy, and $R^{13}$ and $R^{14}$ are independently selected $C_1$-$C_6$ alkyl, (e.g., isopropyl, etc.), or $R^{13}$ and $R^{14}$ may be taken together to form a 5-7 membered ring (e.g., pyrrolidinyl). Examples of such phosphoramidites include but are not limited to O-(di-2-propylamino)(2-cyanoethoxy)phosphoramidite, O-(di-2-propylamino)(methoxy)-phosphoramidite, O-(1-pyrrolidino)(2-cyanoethoxy)phosphoramidite, and O-(dimethylamino)(2-cyanoethoxy) phosphoramidite.

21. "Phosphityl" means a phosphorous (III) moiety.

22. "Solid-supported organic synthesis" means a synthetic approach to making an organic molecule wherein a starting material is first attached to a solid support, then modified by a series of reactions to produce a product, which is subsequently cleaved from the support. A major advantage of solid-supported organic synthesis is that excess reagents and byproducts of the reactions are easily rinsed away, thereby providing a substantially pure product at the conclusion of a multi-step synthesis, the last step of which is cleavage from the solid support. For example, oligonucleotide syntheses often employ a solid support known as controlled pore glass. Peptide synthesis often employs a solid support know as polystyrene-divinylbenzene. Combinatorial chemistry often employs these and other supports.

23. "Polysaccharide" means a straight or branched chain of saccharide moieties. Complex polysaccharides are typically composed of a variety of saccharide moieties and may include one or more amino-hexose or amino-pentose moieties.

24. "Synthon" means a chemical fragment that comprises a portion of the final product of a multi-step organic synthesis. The heteratoms of a synthon may or may not have protecting groups attached, depending on the stage of a synthesis.

25. "Tag" means a chemical fragment that either enables the detection or facilitates the purification of a peptide or oligonucleotide. Examples of tags include fluorescent moieties such as fluorescein, tetramethyrhodamine, tetraethylrhodamine, and dansyl; quencher dyes such as dabsyl, dabcyl, and BBQ-650; biotin and desthiobiotin; photoaffinity groups such as aryl azide and benzophenone, fluorous protecting groups, azides, and alkynes.

Abbreviations of specific terms used in this disclosure:
1. "Ar" means an aryl group, as defined above.
2. "Ac" means acetyl or C(O)CH3.
3. "Boc" means t-butyloxycarbonyl.
4. "Cbz" means benzyloxycarbonyl.
5. "Cmoc" means colorimetric-oxycarbonyl, i.e. the structure of a compound Formula I without the X substituent.
6. "CEP" means 2-cyanoethyloxy-N,N-diisopropylaminophosphityl.
7. "CPG" means controlled pore glass, a solid support that is frequently used for solid-supported oligonucleotide synthesis.
8. "DMT" means bis(4-methoxyphenyl)(phenyl)methyl, also known as dimethoxytrityl.
9. "DMF" means N,N-dimethylformamide.
10. "DNA" means (2'-deoxyribo)nucleic acid.
11. "Fmoc" means (9H-fluoren-9-yl)methoxycarbonyl.
12. "HPLC" means high pressure liquid chromatography, also known as high performance liquid chromatography.
13. "I" means inosine, a ribonucleoside.
14. "i-Pr" means isopropyl, 2-propyl, or $CH(CH_3)_2$.
15. "lcaa" means long chain aminoalkyl, a linker that is attached to CPG for the solid-supported synthesis of oligonucleotides which is well known to those skilled in the art of oligonucleotide synthesis.
16. "Me" means methyl or $CH_3$.
17. "MMT" means (4-methoxyphenyl)diphenylmethyl, also known as monomethoxytrityl.
18. "Ph" means phenyl or $C_6H_5$.
19. "RNA" means ribonucleic acid.
20. "T" means thymidine, a 2'-deoxyribonucleoside.
21. "T5" means an oligonucleotide composed of five thymidines and their associated phosphodiester links.
22. "t-Bu" means tertiary-butyl or $C(CH_3)_3$.
23. "THF" means tetrahydrofuran.
24. "TLC" means thin layer chromatography.
25. "Tr" means triphenylmethyl, also known as trityl.

Some of the compounds in the present invention may exist as stereoisomers, including enantiomers, and diastereomers. Some compounds of the present invention have cycloalkyl groups, which may be substituted at more than one carbon atom, in which case all geometric forms thereof, both cis and trans, and mixtures thereof, are within the scope of the present invention. All of these forms, including (R), (S), epimers, diastereomers, cis, trans, syn, anti, solvates (including hydrates), tautomers, and mixtures thereof, are contemplated in the compounds of the present invention.

DETAILED DESCRIPTION OF THE INVENTION

The present invention provides methods and compositions for use in the synthesis of organic compounds. In particular the present invention provides for protecting groups which are typically calorimetric when cleaved from a reaction product. Despite the popularity of oxycarbonyl protecting groups, triarylmethyl protecting groups, and calorimetric analyses, a calorimetric protecting group that contains both oxycarbonyl and triarylmethyl functionalities would be useful in the art. This combination provides a useful protecting group for heteroatoms. In certain embodiments, the combination has the property of providing a calorimetric signal when cleaved. Both the triarylmethyl group and the oxycarbonyl group are typically stable under basic conditions but are subject to cleavage under acidic conditions, also known as acid deprotection. Cleavage of the triarylmethyl group provides the calorimetric signal that is useful in the monitoring of solid-supported syntheses. The acid sensitivity of illustrative examples of triarylmethyl groups typically follows the order {least acid sensitive . . . $(4-ClPh)_3$-<Tr-<MMT-<DMT- . . . most acid sensitive}. The acid sensitivity of illustrative examples of oxycarbonyl groups typically follows the order {least acid sensitive . . . $—C(CH_3)_2—O_2C—<—C(4-ClPh)_2-O_2C—<—C(Ph)_2-O_2C—$ . . . most acid sensitive}. In certain embodiments both the triarylmethyloxy and the oxycarbonyl group have similar acid sensitivity so that they are both cleaved in a single reaction. In other embodiments, the triarylmethyloxy group and the oxycarbonyl group have different acid sensitivity so that one may be cleaved with mild acid and the other may subsequently be cleaved with stronger acid. Compounds of Formula I may accommodate the range of acid sensitivity that provides a useful protecting group to a variety of synthesis conditions that are commonly encountered in the practice of solid-supported organic syntheses.

General synthetic schemes for preparing compounds of formula I are set forth below.

Schemes

Scheme 1 shows a synthetic route that is useful for preparing compounds of Formula I that are reagents for the installation of Cmoc protecting groups. Treatment of a lactone 1 with an excess of a $C_1$-$C_6$-alkyl Grignard reagent or an aryl Grignard reagent 2 affords a diol 3 which has a primary hydroxyl group at one end and a tertiary hydroxyl group at the other end. The primary hydroxyl group is then selectively protected by treatment with a triarylmethylchloride 4 and a base such as pyridine. Acylation of the remaining tertiary hydroxyl group with a phosgene equivalent affords the Cmoc protecting group reagent.

Scheme 1: Synthesis of a Cmoc Protecting Group Reagent

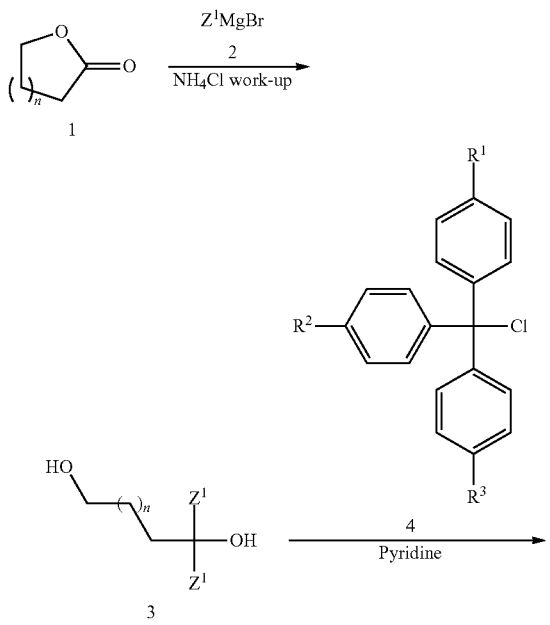

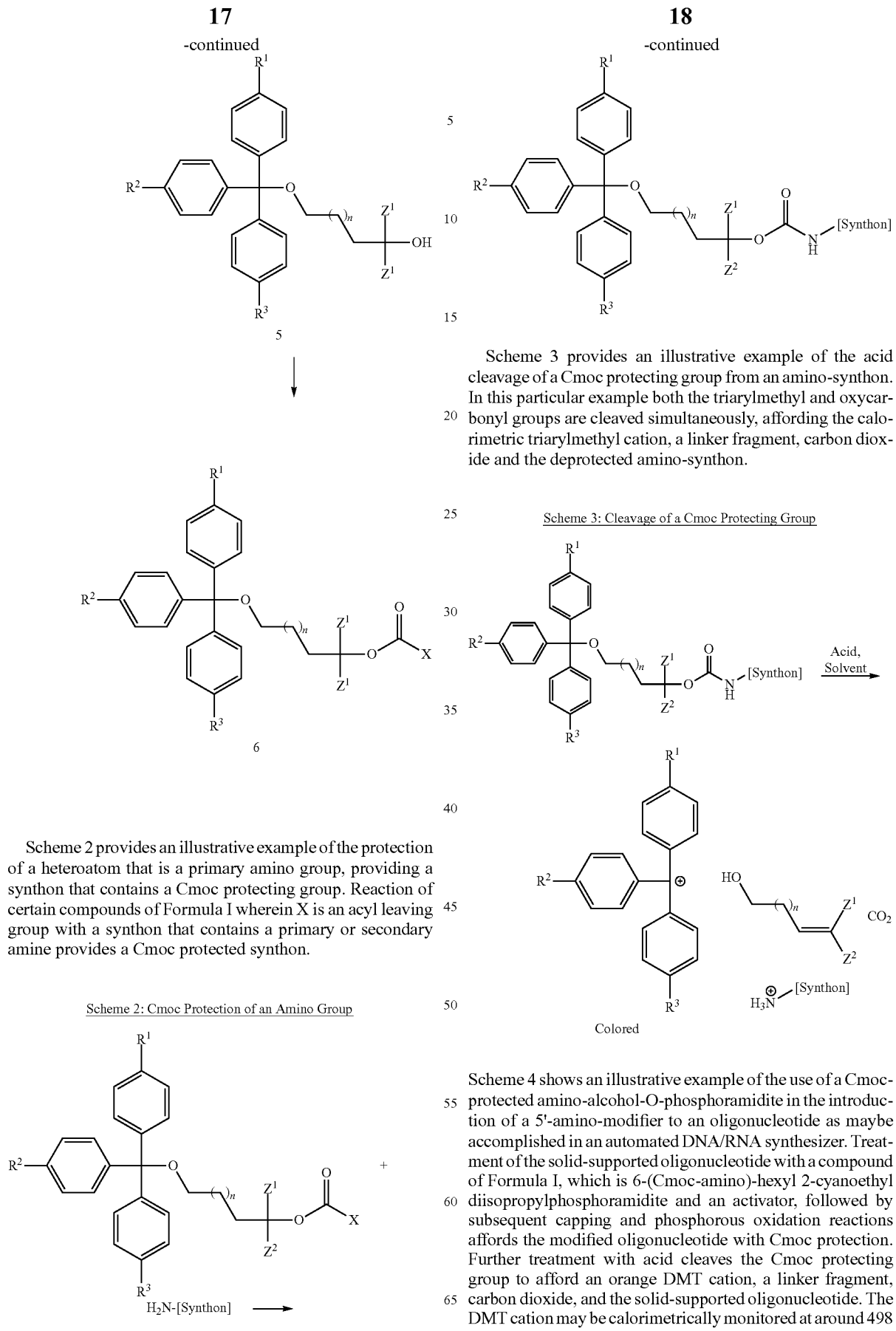

Scheme 3 provides an illustrative example of the acid cleavage of a Cmoc protecting group from an amino-synthon. In this particular example both the triarylmethyl and oxycarbonyl groups are cleaved simultaneously, affording the calorimetric triarylmethyl cation, a linker fragment, carbon dioxide and the deprotected amino-synthon.

Scheme 2 provides an illustrative example of the protection of a heteroatom that is a primary amino group, providing a synthon that contains a Cmoc protecting group. Reaction of certain compounds of Formula I wherein X is an acyl leaving group with a synthon that contains a primary or secondary amine provides a Cmoc protected synthon.

Scheme 4 shows an illustrative example of the use of a Cmoc-protected amino-alcohol-O-phosphoramidite in the introduction of a 5'-amino-modifier to an oligonucleotide as maybe accomplished in an automated DNA/RNA synthesizer. Treatment of the solid-supported oligonucleotide with a compound of Formula I, which is 6-(Cmoc-amino)-hexyl 2-cyanoethyl diisopropylphosphoramidite and an activator, followed by subsequent capping and phosphorous oxidation reactions affords the modified oligonucleotide with Cmoc protection. Further treatment with acid cleaves the Cmoc protecting group to afford an orange DMT cation, a linker fragment, carbon dioxide, and the solid-supported oligonucleotide. The DMT cation may be calorimetrically monitored at around 498 nM by the automated DNA/RNA synthesizer to provide useful information about the installation and deprotection of the 5'-amino-modifier. Since calorimetric analysis of the DMT cation at around 498 nM is a standard method that is engineered into the DNA/RNA synthesizer for measuring the incorporation of each nucleotide as the oligonucleotide is formed, it is convenient to also be able to monitor the incorporation of the 5'-amino-modifier fragment with a DMT cation. In comparing amino protection via a Cmoc protecting group to that of a DMT protecting group that is attached directly to the amino nitrogen atom, there is a distinct stability difference between them. While both would generate a color signal upon cleavage via the release of a DMT cation, the stability of a Cmoc-N linkage to reaction conditions found in a DNA/RNA synthesizer typically is more stable compared to the stability of a DMT-N linkage since DMT tends to cleave prematurely from amines, giving rise to potential side reactions of the amino group and/or lost DMT color signal. The optimal balance between Cmoc-N stability to synthesis conditions and ease of protecting group cleavage can be adjusted according to the needs of the synthesis. As stated previously, variation of $Z^1$ and $Z^2$ allows for fine tuning of the acid sensitivity of a compound of Formula I. As shown in Scheme 4 below, the use of Ar groups such as phenyl and 4-chlorophenyl for $Z^1$ and $Z^2$ is can be employed with regard to attaining the proper stability for the 5'-amino-modifier application as shown in this illustrative example.

Scheme 4: Use of a Cmoc-Protected 5'-Amino-modifier in Oligonucleotide Synthesis

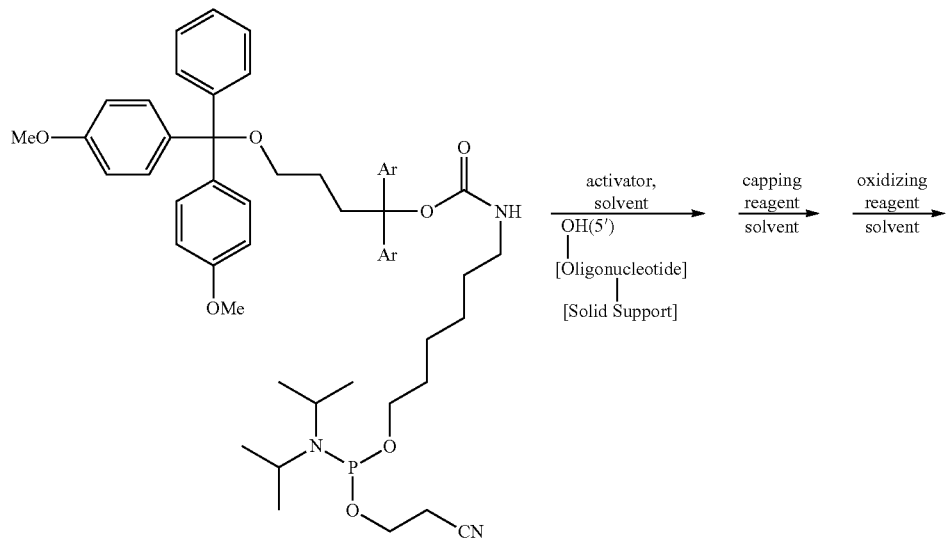

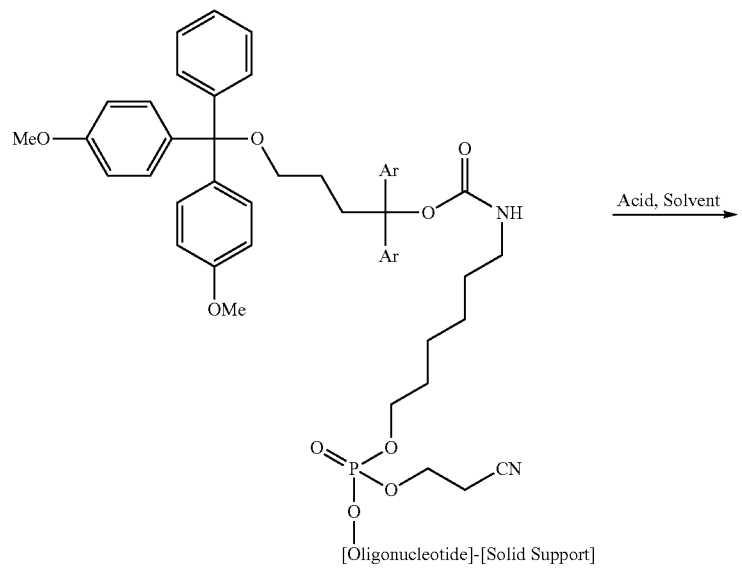

-continued

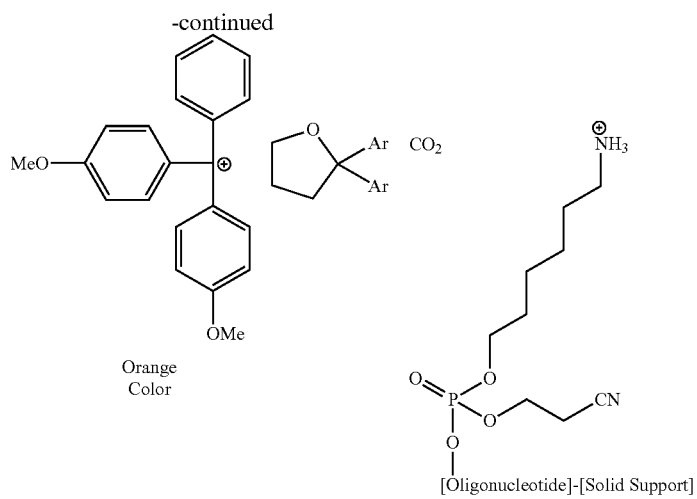

Orange Color

Scheme 5 shows an illustrative example of the use of a Cmoc protected 5'-amino-nucleoside-O-phosphoramidite in the 5'-amino-modification of an oligonucleotide in an automated DNA/RNA synthesizer. Treatment of the solid-supported oligonucleotide with a compound of Formula I, which is a Cmoc protected 5'-amino-nucleoside-O-phosphoramidite and an activator, followed by subsequent capping and phosphorous oxidation reactions affords the oligonucleotide with a 5'-Cmoc-amino moiety. Further treatment with acid cleaves the Cmoc protecting group to afford an orange DMT cation, a linker fragment, carbon dioxide, and the solid-supported oligonucleotide. The DMT cation may be calorimetrically monitored at around 498 nM by the automated DNA/RNA synthesizer to provide useful information about the installation and deprotection of the 5'-aminomodifier. The properties of Cmoc protection/deprotection in Scheme 5 are generally the same as those described previously in the description of Scheme 4.

Scheme 5: Use of a Cmoc-Protected 5'-Amino-nucleoside-3'-O-phosphoramidite in Oligonucleotide Synthesis

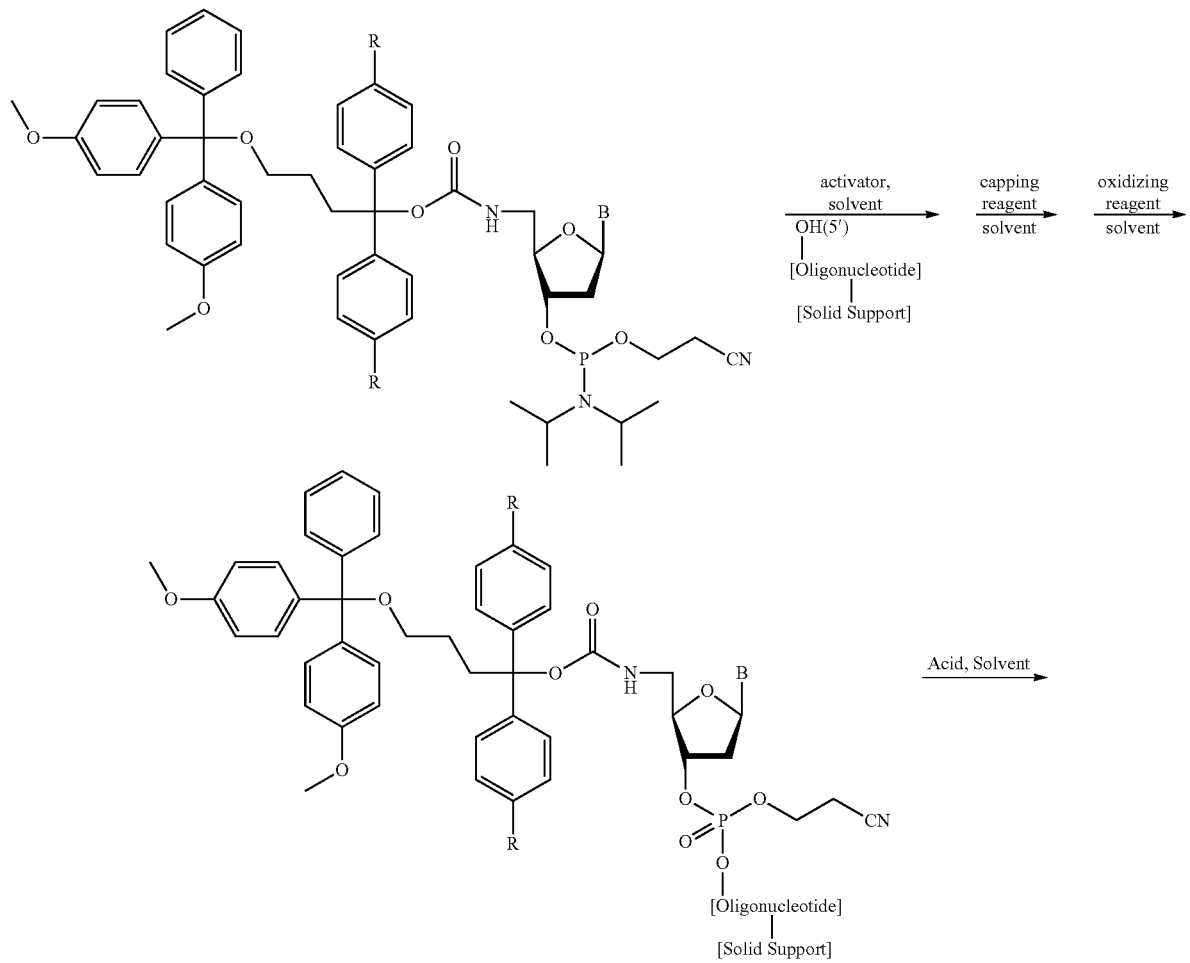

-continued

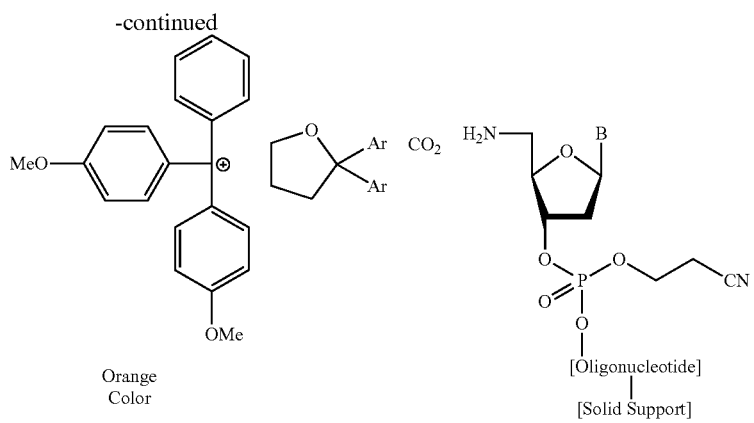

Orange
Color

Scheme 6 below shows an illustrative example of the use of Cmoc-protected amino-acids in an automated peptide synthesizer. The amino groups of the amino-acids used to build the peptide are protected with a Cmoc protecting group. The Cmoc-amino-acid with a free carboxylic acid and a solid-supported amino-acid with a free amino group are treated with one of the many coupling reagents known to those skilled in the art of peptide synthesis, thereby forming a Cmoc-protected dipeptide on the solid support. Treatment with acid in a solvent, simultaneously cleaves the triarylmethyl and oxycarbonyl ends of the Cmoc protecting group affording a colored triaryl cation, a linker fragment, carbon dioxide and the solid-supported dipeptide with a free amino terminus. Repetition of this sequence using other Cmoc-protected amino acids affords a solid-supported peptide. The synthesizer measures the color liberated at each acid deprotection step, thereby confirming the success of the coupling step and the deprotection step. This confirmation is not possible when Boc-protected amino-acids are used since there is no color generated upon the cleavage of a Boc protecting group. Thus the Cmoc method has a distinct advantage over the Boc method for automated peptide synthesis.

Scheme 6. Use of Cmoc-protected amino acids in peptide synthesis

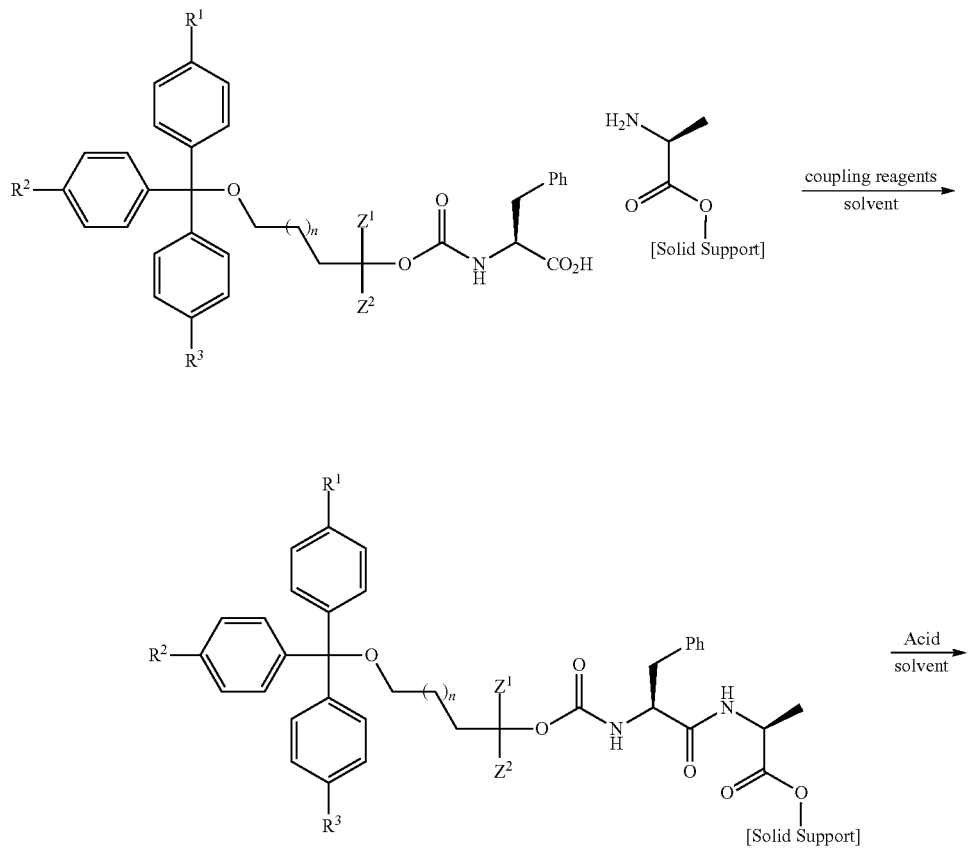

-continued

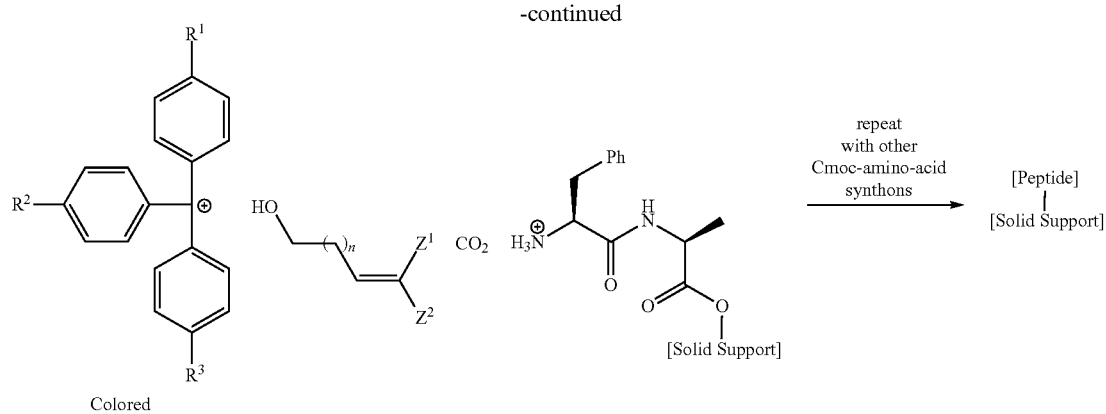

Scheme 7 below shows an illustrative example of the use of Cmoc protecting groups in automated, solid-supported combinatorial chemistry. In the first step, a set of mono-Cmoc-protected diamines is loaded onto the phenacyl chloride-containing solid support. The Cmoc group is then cleaved with acid, thereby generating a color that can be monitored to verify successful loading and deprotection. A set of active esters are then used to acylate the each of the deprotected amines on the solid support. In this illustrative example 3 (solid-supported Cmoc-diamines) combined with 3 (active esters) affords 9 (solid-supported diamides).

phorsulfonic acid, methanesulfonic acid, and the like. Acid addition salts of the basic compounds may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents.

Acceptable base addition salts may be formed by contacting the parent acid with a sufficient amount of an inorganic

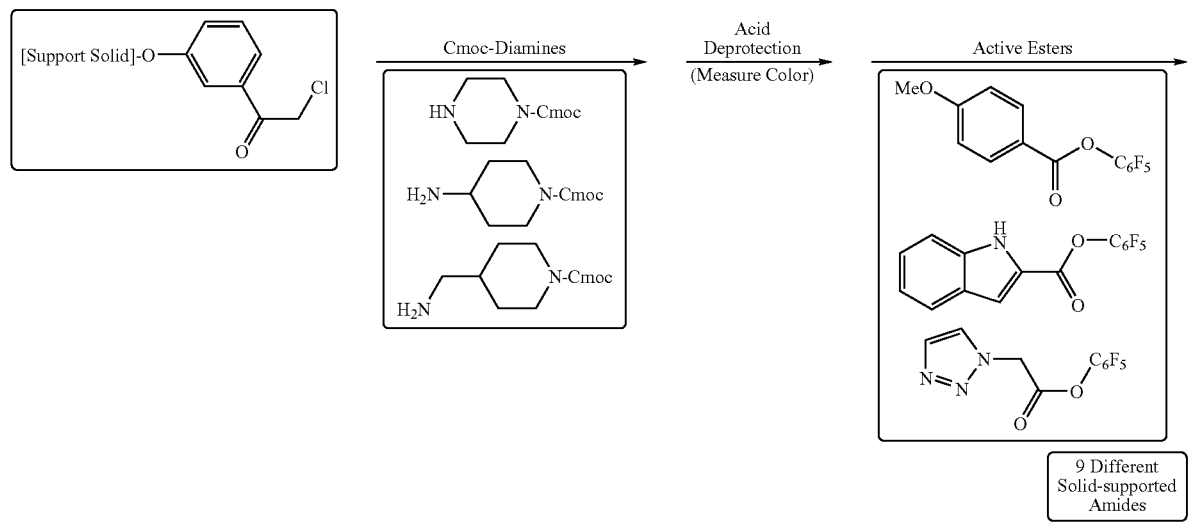

Acceptable Salts and Solvates

Some of the compounds to be used in the present invention may exist in unsolvated forms as well as solvated forms, including hydrated forms.

Some of the compounds of the present invention (e.g., compounds of Formula I) are capable of further forming acceptable salts, including acid addition and/or base salts.

Acceptable acid addition salts of the compounds of Formula I include salts derived from inorganic acids such as hydrochloric, hydrobromic, phosphoric, sulfuric, and the like, as well as the salts derived from organic acids, such as acetic acid, benzoic acid, citric acid, D-tartaric acid, L-tartaric acid, benzenesulfonic acid, toluenesulfonic acid, cambase such as ammonia and the hydroxides and alkoxides of inorganic metals including sodium, potassium, lithium, calcium, barium hydroxide, and the like to produce the salt in the conventional manner. Other acceptable base addition salts may be formed by contacting the parent acid with organic bases diethylamine, triethylamine, diethanolamine, ethanolamine, cyclohexylamine, dicyclohexylamine, (+)α-methylbenzylamine, (−)α-methylbenzylamine, isopropylamine, diisopropylamine, ethylenediamine (ethane-1,2-diamine), N,N-dimethyl-ethylenediamine, guanidine, tetramethylguanidine, and the like to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents.

EXAMPLES

Intermediate 1

4-Methylpentane-1,4-diol

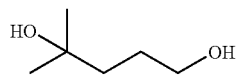

A solution of butyrolactone (5.5 g, 63.8 mmol) in anhydrous THF (250 mL) was chilled to −78° C. under nitrogen atmosphere. Methyllithium (1.6M in ether, 100 mL, 160 mmol) was added via syringe at a rate that kept the reaction temperature below −40° C. After the addition was complete, the cold bath was removed and the reaction mixture was allowed to warm to room temperature for 6 hours. The solution was then re-cooled to 10° C. on an ice bath before the addition of acetic acid (10 mL) dropwise to quench the reaction. The resulting suspension was diluted with an equal volume of ethyl acetate and filtered. Evaporation of solvent from the filtrate afforded crude 4-methylpentane-1,4-diol as an oil. Chromatography on silica gel, eluting with 1:1 ethyl acetate-hexane gave 3.7 g of pure 4-methylpentane-1,4-diol. MS (EI+): 119 (M+1); 101 (M-H$_2$O+1).

Intermediate 2

5-(Bis(4-methoxyphenyl)(phenyl)methoxy)-2-methylpentan-2-ol

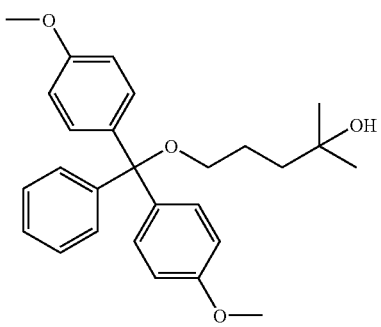

A solution of Intermediate 1 (3.7 g, 31.4 mmol) in dichloromethane (200 mL) was treated with N,N-diisopropyl-ethylamine (4.1 g, 31.7 mmol) and DMT-Cl, (10.5 g, 31.4 mmol) and stirred at room temperature overnight. The reaction mixture was then further diluted with dichloromethane (300 mL) and washed with water (2×500 mL). The organic layer was dried over anhydrous sodium sulfate, filtered, and evaporated to a foam. Chromatography on silica gel, eluting with a 0-2% gradient of isopropanol in dichloromethane gave 4.4 g of the mono-DMT-protected diol. MS (EI+): 421 (M+1).

Intermediate 3

1,1-diphenylbutan-1,4-diol

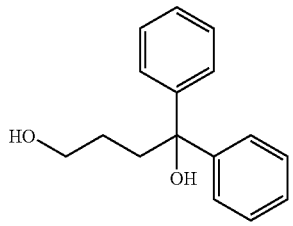

A solution of butyrolactone (10.5 g, 122 mmol) in anhydrous THF (500 mL) was chilled to −78° C. under nitrogen atmosphere. Phenylmagnesium bromide (3M in ether, 100 mL, 300 mmol) was added via syringe at a rate that keeps the reaction temperature below −40° C. After the addition was complete, the reaction was stirred at −78° C. for two hours then the cold bath was removed and the reaction mixture was allowed to warm to room temperature overnight. The solution was then re-cooled to 10° C. on an ice bath before adding 2N aqueous ammonium chloride (200 mL) to quench the reaction. The resulting mixture was diluted with ethyl acetate (1 L) and the organic layer was separated, washed with saturated aqueous sodium chloride, dried over anhydrous sodium sulfate and filtered. Evaporation of solvent from the filtrate afforded crude 1,1-diphenylbutan-1,4-diol as an oil, which was purified by chromatography on silica gel, eluting with a gradient of 50% to 60% ethyl acetate in hexane. Evaporation of solvents gave a colorless solid that was triturated with hexane and collected by filtration to afford 18.2 g of pure 1,1-diphenylbutan-1,4-diol. MS (EI+): 243 (M+1); 225 (M-H$_2$O+1).

Intermediate 4

1,1-bis(4-chlorophenyl)butane-1,4-diol

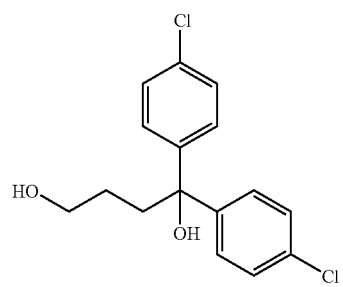

Substitution of 4-chlorophenylmagnesium bromide for phenylmagnesium bromide in the method of Intermediate 3 afforded 1,1-bis(4-chlorophenyl)butane-1,4-diol. MS (EI+): 313, 312, 311 (M+1).

Intermediate 5

4-(bis(4-methoxyphenyl)(phenyl)methoxy)-1,1-diphenylbutan-1-ol

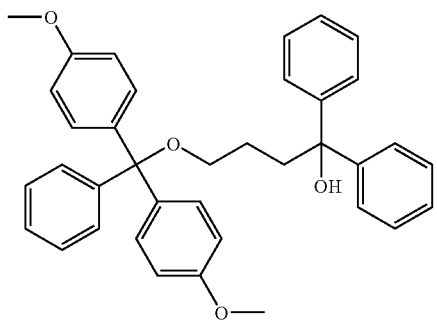

A solution of Intermediate 3 (15 g, 61.9 mmol) in dichloromethane (300 mL) was chilled to 0° C. and then treated with N,N-diisopropyl-ethylamine (8 g, 61.9 mmol). DMT-Cl (21 g, 61.9 mmol) was then added in six portions over 30 minutes. The reaction was allowed to warm to room temperature over 1 hour then stirred 1 hour more. The resulting solution was then washed with water (2×150 mL) and the organic layer was dried over anhydrous sodium sulfate, filtered, and evaporated. The residue was purified by chromatography on silica gel, eluting with 5:1 hexane-ethyl acetate. Evaporation of solvents afforded 4-(bis(4-methoxyphenyl)(phenyl)methoxy)-1,1-diphenylbutan-1-ol (33.4 g) as a colorless foam. $^1$H-NMR (CDCl$_3$) δ: 7.43 (t, 6H); 7.35-7.18 (m, 13H); 6.81 (d, 4H); 3.79 (s, 6H); 3.13 (t, 2H); 2.83 (s, 1H); 2.35 (m, 2H); 1.64 (m, 2H).

Intermediate 6

4-(bis(4-methoxyphenyl)(phenyl)methoxy)-1,1-bis(4-chlorophenyl)butan-1-ol

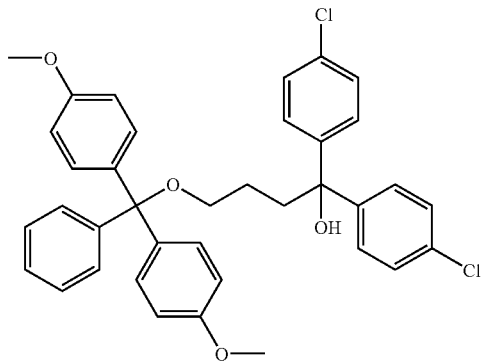

Substitution of equimolar quantity of Intermediate 4 for Intermediate 3 in synthesis of Intermediate 5 afforded the title product as a colorless foam. MS (EI+): 313, 312, 311 (M+1).

Intermediate 7

1,1-Bis(4-chlorophenyl)hexan-1-ol

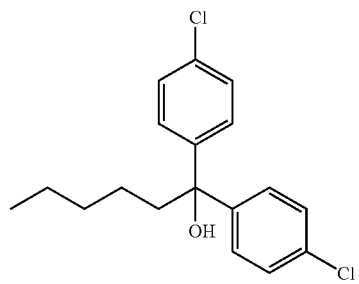

Using the method of Intermediate 4, a solution of methyl hexanoate in THF is treated with 4-chlorophenylmagnesium bromide to afford 1,1-bis(4-chlorophenyl)hexan-1-ol. MS (EI+): 322, 323, 324 (M+1)

Example 1

5-(Bis(4-methoxyphenyl)(phenyl)methoxy)-2-methylpentan-2-yl 1H-imidazole-1-carboxylate

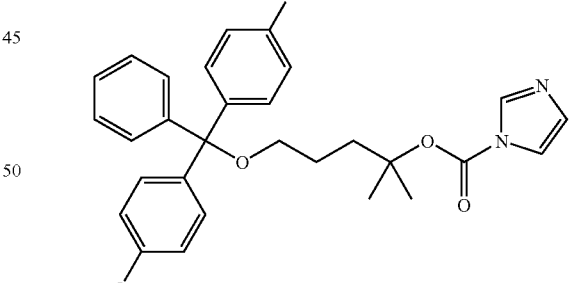

A suspension of sodium hydride (5.2 mmol) in THF (40 mL) was treated dropwise with a solution of Intermediate 2 (1.48 g 3.5 mmol) in DMF (40 mL) and the mixture was stirred at room temperature for 1 hour. The resulting solution was treated with 1,1'-carbonyldiimidazole (0.9 g, 5.6 mmol) and stirred 1 hour further at room temperature. TLC (silica gel on glass, hexane-ethyl acetate 1:1) showed complete conversion of the starting alcohol (R$_f$=0.8) to the imidazolide (R$_f$=0.7). It is usually convenient to use this product in situ without isolation and rigorous characterization.

Example 2

(S)-Methyl 2-((5-(bis(4-methoxyphenyl)(phenyl)-methoxy)-2-methylpentan-2-yloxy)carbonylamino)-3-phenylpropanoate

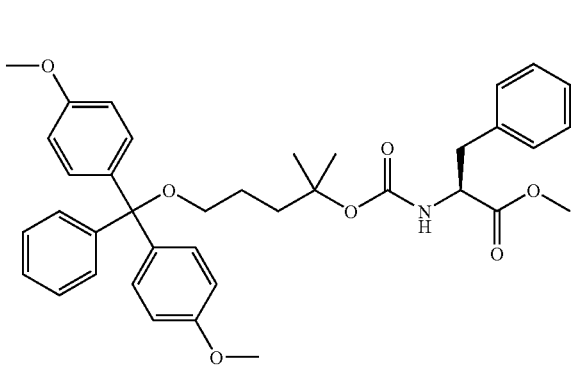

A solution composed of L-phenylalanine methyl ester hydrochloride (1.4 g, 6.1 mmol), diisopropylethylamine (1.1 mL, 6.2 mmol), and N,N-dimethylformamide (40 mL) was added to the solution of Example 1. The reaction was stirred overnight at room temperature. The solvents were evaporated at reduced pressure, and then the residue was partitioned between ethyl acetate and water. The organic layer was washed with saturated aqueous sodium chloride, dried over sodium sulfate, and filtered. The solvents were evaporated once again. Chromatography on silica gel eluting with hexane-ethyl acetate 70:30 afforded purified Cmoc-protected phenylalanine methyl ester. MS (EI+): 626 (M+1).

Example 3

(S)-2-((5-(bis(4-methoxyphenyl)(phenyl)methoxy)-2-methylpentan-2-yloxy)carbonylamino)-3-phenyl-propanoic acid

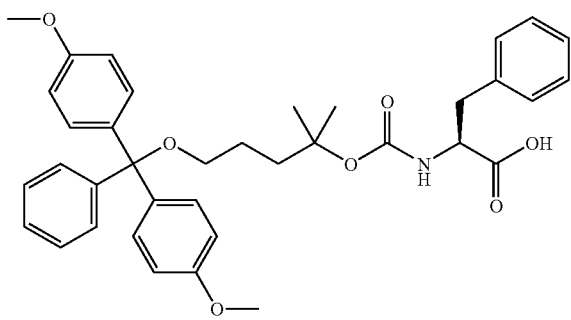

A solution of Example 2 (625 mg, 1 mmol), tetrahydrofuran (7 mL) and methanol (3 mL) was treated with 1N sodium hydroxide (1 mL, 1 mmol). The reaction mixture was stirred at room temperature for 6 hours then treated with 1N hydrogen chloride (1 mL, 1 mmol). The reaction mixture was partitioned between ethyl acetate and water. The organic layer was washed with saturated aqueous sodium chloride, dried over ahydrous magnesium sulfate, and filtered. Evaporation of solvent afforded Cmoc-protected phenylalanine of sufficient purity for use in solid-supported peptide synthesis. MS (EI−): 610 (M−1).

Example 5

4-(bis(4-methoxyphenyl)(phenyl)methoxy)-1,1-diphenylbutyl 6-hydroxyhexylcarbamate

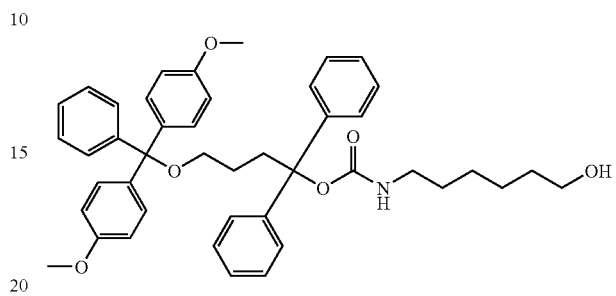

A solution of Intermediate 5 (1.6 g, 2.96 mmol) in THF (30 mL) was treated with portions of sodium hydride (60% suspension in mineral oil, 0.18 g, 4.5 mmol), allowing the gas evolution to subside between successive additions. The resulting solution was stirred for 1 hour then a solution of 1,1'-carbonyldiimidazole (0.96 g, 5.9 mmol) in DMF (30 mL) was added. This solution was stirred 1 hour at room temperature before adding a solution of 6-aminohexan-1-ol (1.7 g, 14.8 mmol) in dichloromethane (60 mL). The reaction was stirred 1 hour more at room temperature then concentrated at reduced pressure. The residue was partitioned between ethyl acetate (300 mL) and water (100 mL). The organic layer was separated, washed with water (2×50 mL), washed with saturated aqueous sodium chloride (100 mL), dried over anhydrous sodium sulfate, filtered, and evaporated at reduced pressure. The residue was purified by chromatography on silica gel, eluting with 1:1 hexane-ethyl acetate. Evaporation of solvents gave a gum that was dissolved in dichloromethane and evaporated again at reduced pressure to afford a colorless foam. Further drying in vacuo afforded 4-(bis(4-methoxyphenyl)(phenyl)methoxy)-1,1-diphenylbutyl 6-hydroxyhexylcarbamate. $^1$H-NMR (CDCl3) δ: 7.40-7.16 (m, 19H); 6.79 (d, 4H); 4.85 (t, 1H); 3.79 (s, 6H); 3.54 (t, 2H); 3.08 (q, 2H); 3.01 (t, 2H), 2.81 (m, 2H); 1.49 (m, 7H); 1.27 (m, 4H).

Example 6

4-(bis(4-methoxyphenyl)(phenyl)methoxy)-1,1-bis(4-chlorophenyl)butyl 6-hydroxyhexylcarbamate

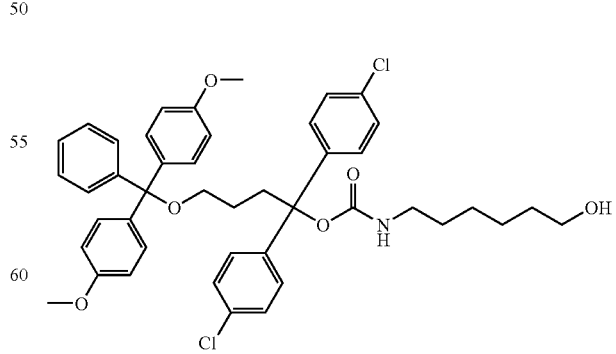

Substitution of equimolar quantity of Intermediate 6 for Intermediate 5 in Example 5 afforded the title product as a colorless foam. MS (EI+): 758, 757, 756 (M+1).

Example 7

4-(bis(4-methoxyphenyl)(phenyl)methoxy)-1,1-bis(4-chlorophenyl)butyl ((2R,3R,5R)-3-hydroxy-5-(6-oxo-1H-purin-9(6H)-yl)tetrahydrofuran-2-yl)methyl-carbamate

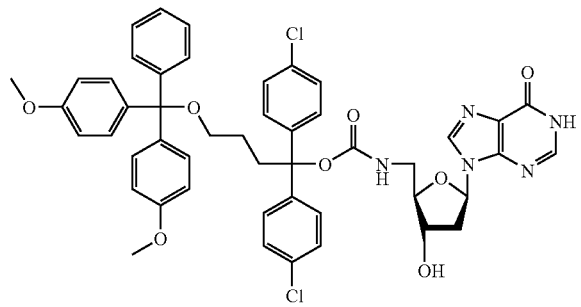

A solution of Intermediate 6 (614 mg, 1.0 mmol) in anhydrous THF (6 mL) was added dropwise to a 5° C. suspension of sodium hydride (60% suspension in mineral oil, 60 mg, 1.5 mmol) in anhydrous THF (4 mL) under nitrogen atmosphere. After the gas evolution ceases, the cold bath was removed and the resulting solution was stirred for 1 hour before adding a solution of 1,1'-carbonyldiimidazole (250 mg, 1.3 mmol) in DMF (30 mL) was added. This solution was stirred 1 hour at room temperature before adding a solution of 5'-amino-2',5'-dideoxyinosine hydrochloride (288 mg, 1.0 mmol) in DMF (10 mL). The reaction was stirred 1 hour more at room temperature then concentrated at reduced pressure. The residue was partitioned between ethyl acetate (150 mL) and water (50 mL). The organic layer was separated, washed with water (2×50 mL), washed with saturated aqueous sodium chloride (50 mL), dried over anhydrous sodium sulfate, filtered, and evaporated at reduced pressure. The residue was purified by chromatography on silica gel, eluting with dichloromethane containing a gradient of 1-5% methanol. Evaporation of solvents from product containing fractions gave a gum that was dissolved in dichloromethane and evaporated again at reduced pressure to afford a colorless foam. Further drying in vacuo afforded 4-(bis(4-methoxyphenyl)-(phenyl)methoxy)-1,1-bis(4-chlorophenyl)butyl ((2R,3R,5R)-3-hydroxy-5-(6-oxo-1H-purin-9(6H)-yl)tetrahydrofuran-2-yl)methylcarbamate. MS (EI+) 892, 891, 890 (M+1).

Example 8

4-(bis(4-methoxyphenyl)(phenyl)methoxy)-1,1-diphenylbutyl 6-((2-cyanoethoxy)(diisopropylamino)phosphinooxy)-hexylcarbamate ("Cmoc-$C_6$-amino-modifier-CEP")

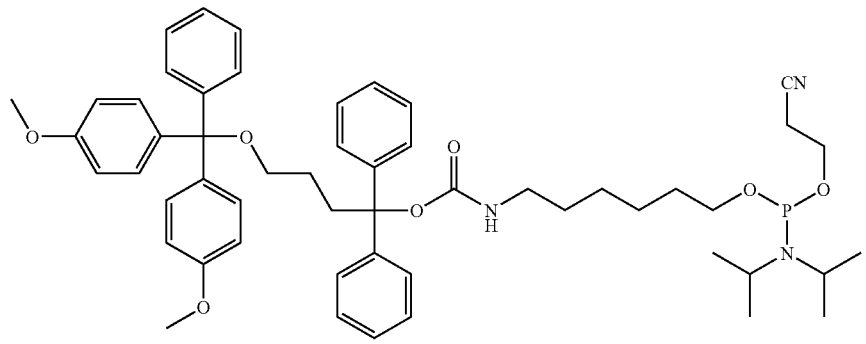

A solution of Example 5 (3.72 g, 5.4 mmol) in anhydrous THF (35 mL) was treated with diisopropylethylamine (1.13 mL, 6.5 mmol) under nitrogen atmosphere. The resulting solution was treated with 3-(chloro(diisopropylamino)phosphinooxy)-propanenitrile (1.3 mL, 5.9 mmol). After stirring for 20 minutes at room temperature, the resulting slurry was filtered and the filtrate was loaded onto a bed of silica gel (100 g) that was wetted with a hexane-triethylamine (97:3). Further elution with hexane-ethyl acetate (2:1) afforded purified product (4.0 g) as a colorless foam upon evaporation of solvents and drying under vacuum. $^1$H-NMR (CD$_3$CN) δ: 7.37 (m, 6H); 7.28 (m, 6H); 7.23 (d, 4H); 7.18 (q, 3H); 6.82 (d, 4H); 5.89 (t, 1H); 3.76 (s, 6H); 3.73 (m, 2H); 3.59 (m, 4H); 2.97 (m, 4H); 2.84 (m, 2H); 2.58 (t, 2H); 1.57 (m, 2H); 1.40 (m, 4H); 1.28 (m, 4H); 1.13 (4s, 12H). MS (EI+): 927 (M+K); 911 (M+Na).

Example 9

4-(bis(4-methoxyphenyl)(phenyl)methoxy)-1,1-bis(4-chlorophenyl)butyl 6-((2-cyanoethoxy)(diisopropylamino)phosphinooxy)-hexylcarbamate ("dichloro-Cmoc-C$_6$-aminomodifier-CEP")

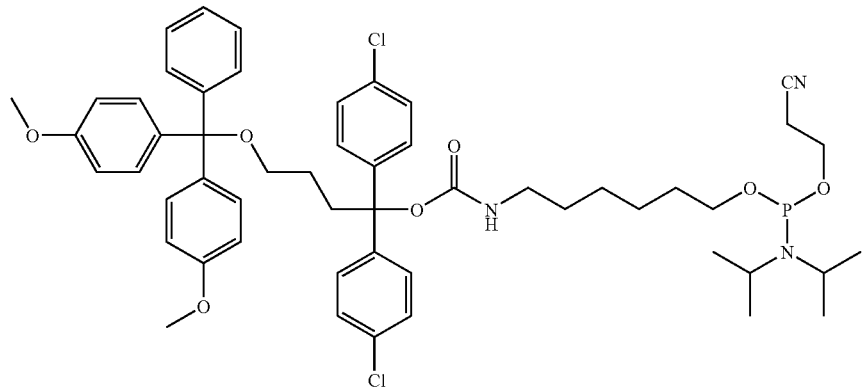

A solution of Example 6 (2.5 g, 3.3 mmol) in anhydrous dichloromethane (20 mL) was treated with 3-(bis(diisopropylamino)phosphinooxy)-propanenitrile (1.2 mL, 3.9 mmol) under nitrogen atmosphere. The resulting solution was treated with a solution of trifluoroacetic acid (0.25M) and 1-methylimidazole (0.5M) in dichloromethane (4.8 mL). The resulting mixture was stirred at room temperature for 2 hours. The reaction mixture was partitioned between dichloromethane (125 mL) and cold water (150 mL). The organic layer was separated and washed again with water (150 mL). The organic layer was separated, dried over anhydrous sodium sulfate, filtered and concentrated at reduced pressure. The concentrate was loaded onto a bed of silica gel (100 g) that was wetted with hexane-triethylamine (97:3). Further elution with hexane-ethyl acetate (2:1) afforded purified product (2.3 g) as a colorless foam upon evaporation of solvents and drying under vacuum. MS (EI+): 996, 995, 994 (M+K); 980, 979, 978 (M+Na).

Example 10

4-(bis(4-methoxyphenyl)(phenyl)methoxy)-1,1-bis(4-chlorophenyl)butyl ((2R,3R,5R)-3-((2-cyanoethoxy)(diisopropylamino)-phosphinooxy)-5-(6-oxo-1H-purin-9(6H)-yl)tetrahydrofuran-2-yl)-methylcarbamate (dichloro-Cmoc-5'-amino-2',5'-dideoxy-1-CEP")

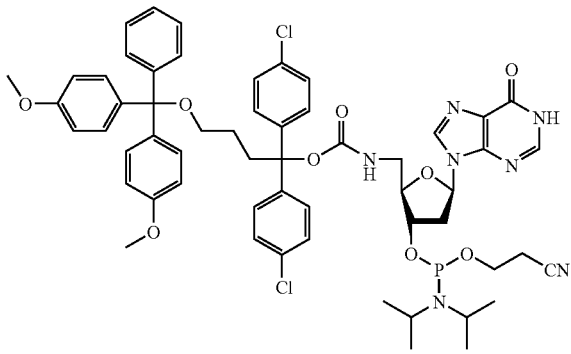

A solution of Example 7 (891 mg, 1.0 mmol) in anhydrous dichloromethane (20 mL) was treated with 3-(bis(diisopropylamino)phosphinooxy)-propanenitrile (0.37 mL, 1.2 mmol) under nitrogen atmosphere. The resulting solution was treated with a solution of trifluoroacetic acid (0.25M) and 1-methylimidazole (0.5M) in dichloromethane (2.0 mL). The resulting mixture was stirred at room temperature for 16 hours. The reaction mixture was added dropwise to vigorously stirred pentane (400 mL). The resulting precipitate was collected by filtration and rinsed with pentane. The moist product was dissolved in ethyl acetate (50 mL) and washed twice with water (2×30 mL). The organic layer was separated, dried over anhydrous sodium sulfate and filtered and concentrated at reduced pressure. The concentrate was loaded onto a bed of silica gel (4 g) that was wetted with ethyl acetate-dichloromethane (75:25). Further elution with ethyl acetate afforded purified product as a colorless foam upon evaporation of solvents and drying under vacuum. MS (EI+): 1130, 1129, 1128 (M+K); 1114, 1113, 1112 (M+Na).

Example 11

1,1-Bis(4-chlorophenyl)hexyl 1H-imidazole-1-carboxylate

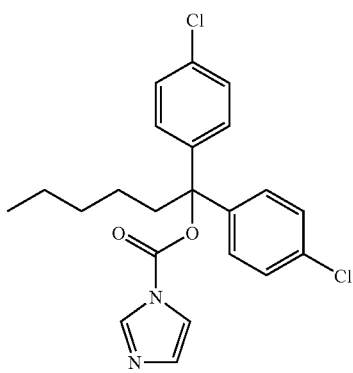

Using the method of Example 1, Intermediate 7 is treated with sodium hydride, followed by 1,1'-carbonyldiimidazole to afford a solution of the title product. It is usually convenient to use this product in situ without isolation and rigorous characterization.

Use Example 1

($C_6$-Aminomodifier)-$T_6$-lcaa-CPG and (DMT-$C_6$-Aminomodifier)-$T_6$

Using a Millipore Expedite (8900 series) nucleic acid synthesis system (Billerica, Mass.), freshly prepared reagent solutions installed as follows were installed in the reagent bottles as follows:
Wash A—anhydrous acetonitrile
Deblock—3% Trichloroacetic acid in anhydrous dichloromethane
Oxidizer—0.02M iodine in tetrahydrofuran/water/pyridine
Capping reagent A—acetic anhydride/anhydrous tetrahydrofuran
Capping reagent B—16% 1-methylimidazole in anhydrous tetrahydrofuran/pyridine
Wash reagent—anhydrous acetonitrile
Activator—0.25M 5-ethylthiotetrazole in anhydrous acetonitrile
Amidites: Thymidine-CEP and Example 9 (0.067M solutions in anhydrous acetonitrile)

The reagent lines were purged and pumps primed. Two synthesis columns containing 200 nM of DMT-protected-Thymidine-CPG were installed.
The instrument run parameters were then set as follows:
Column—1
Sequence—TTTTTTX (wherein T denotes a Thymidine residue and X denotes an Example 9 residue)
Protocol—CYCLE T (a 23 step protocol for reagent additions, reaction times, and washes known to be optimized for each coupling of Thymidine-CEP, as provided in the synthesizer software)
Final DMT—OFF (The DMT of the X residue is subjected to Deblock solution)
Column—2
Sequence—TTTTTTX
Protocol—CYCLE T
Final DMT—ON (The DMT of the X residue is not subjected to Deblock solution)

($C_6$-Aminomodifier)-$T_6$-lcaa-CPG was synthesized in column 1 using CYCLE T conditions for each T residue and for the final coupling of Example 9. The output of the calorimetric monitoring of each deblock step was recorded by the synthesizer's computer. The integrated values for each of the 7 deblock steps were 2.17, 2.14, 2.16, 2.21, 2.20, 2.18 and 1.8 (all×$10^6$). These calorimetric readings are consistent with the successful synthesis of ($C_6$-Aminomodifier)-$T_5$-lcaa-CPG.

Similarly DMT-$C_6$-Aminomodifier-$T_6$-lcaa-CPG was synthesized in column 2. This column was further subjected to treatment 28-30% ammonium hydroxide for 18 hours at room temperature in order to deprotect the phosphate moieties and cleave the oligonucleotide from the CPG support. The resulting solution of DMT-$C_6$-Aminomodifier-$T_6$ was sparged with a stream of nitrogen to expel excess ammonia then diluted with an equal volume of acetonitrile. Reversed phase HPLC analysis on a Waters Spherisorb ODS-2 column (150×4.6 mm) eluting at 1.0 mL/min with a gradient of 5 to 80% acetonitrile in 0.1M triethylammonium acetate showed a peak integration ratio for $T_6$ (retention time approximately 11.4 min, equal to a reference sample) to DMT-$C_6$-Aminomodifier-$T_6$ (retention time approximately 35 min, consistent with a DMT-on oligo) that is 2.1 to 97.9, further confirming the successful coupling of Example 9 at the 5'-end of the oligonucleotide.

Use Example 2

$T_5$-($C_6$-Aminomodifier)-$T_5$-lcaa-CPG

Using analogous methods to those described in Use Example 1, a Millipore Expedite (8900 series) nucleic acid synthesis system was used to prepare an oligonucleotide with Example 9 coupled into the middle of a sequence of 10 thymidines. The output of the calorimetric monitoring of each deblock step was recorded by the synthesizer's computer. The integrated values for each of the 11 deblock steps were 2.14, 2.16, 2.21, 2.20, 2.18, 1.8, 1.88, 1.88, 1.86, 1.87 and 1.93 (all×$10^6$). These calorimetric readings are consistent with the successful synthesis of $T_5$-($C_6$-Aminomodifier)-$T_5$-lcaa-CPG.

It is therefore intended that the foregoing detailed description be regarded as illustrative rather than limiting, and that it be understood that it is the following claims, including all equivalents, that are intended to define the spirit and scope of this invention.

What is claimed is:
1. A compound of Formula I

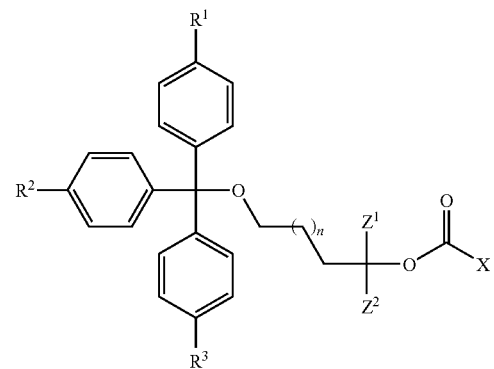

wherein:
$R^1$, $R^2$, and $R^3$ are each independently H, Br, Cl, Fl, R, or OR wherein R is $C_1$-$C_6$-alkyl;
X is selected from the group consisting of an acyl-leaving group, a $C_1$-$C_6$-alkyl ester of an amino acid, an active ester of an amino acid, an amino acid, an amino alcohol, an amino ether, an amino alcohol-O-phosphoramidite, an amino-nucleoside, an amino-nucleoside-O-phosphoramidite, and a diamine;
n is an integer that is selected from 0 to 8;
$Z^1$ and $Z^2$ are each independently $C_1$-$C_6$-alkyl, or aryl;
or a salt thereof.

2. The compound of claim 1, wherein $R^1$, $R^2$ and $R^3$ are each independently H, Cl, or $CH_3O$, and $Z^1$ and $Z^2$ are identical.

3. The compound of claim 1, wherein $R^1$ is H, $R^2$ and $R^3$ are both $CH_3O$, and $Z^1$ and $Z^2$ are identical.

4. The compound of claim 1, wherein $Z^1$ and $Z^2$ are $CH_3$, Ph, or 4-Cl-Ph.

5. The compound of claim 1, wherein X is an acyl-leaving group.

6. The compound of claim 1, wherein X is a $C_1$-$C_6$-alkyl ester of an amino-acid.

7. The compound of claim 1, wherein X is an active ester of an amino-acid.

8. The compound of claim 1, wherein X is an amino-acid.

9. The compound of claim 1, wherein X is an amino-alcohol.

10. The compound of claim 1, wherein X is an amino-ether.

11. The compound of claim 1, wherein X is an amino-alcohol-O-phosphoramidite.

12. The compound of claim 1 wherein X is an amino-nucleoside.

13. The compound of claim 1, wherein X is an amino-nucleoside-O-phosphoramidite.

14. The compound of claim 1, wherein X is a diamine.

15. The compound of claim 1, wherein $R^1$ is H, $R^2$ and $R^3$ are $OCH_3$, X is 1-imidazolyl, n is 1, and $Z^1$ and $Z^2$ are selected from the group consisting of $CH_3$, Ph, or 4-Cl-Ph.

16. The compound of claim 1 that is shown in formula II below wherein R is H or Cl:

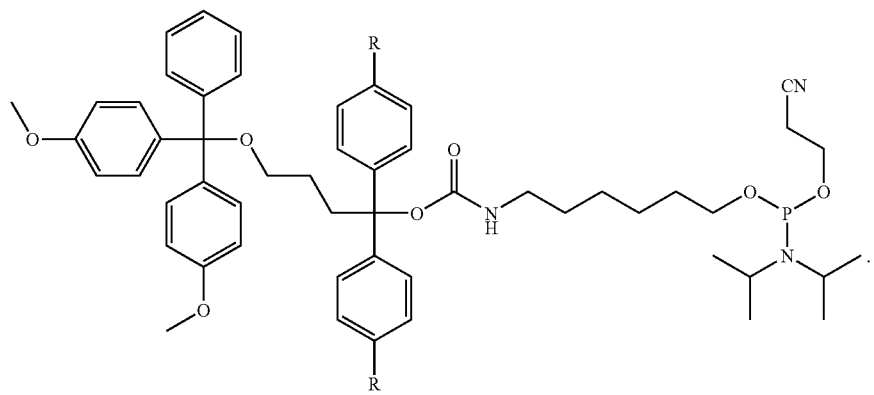

II

17. The compound of claim 1 that is shown in formula III below

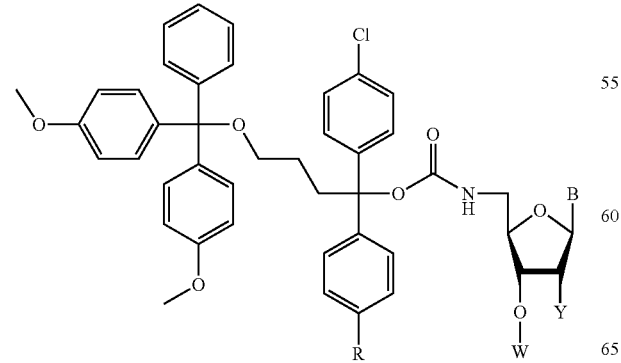

III wherein:

R is H or Cl;

B is selected from the group consisting of:

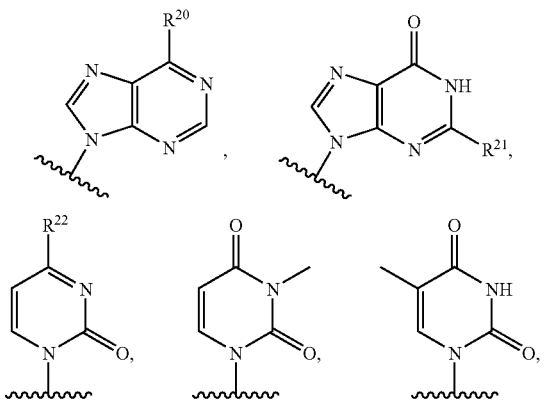

-continued

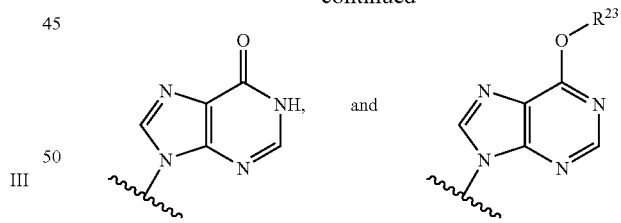

$R^{20}$ is selected from the group consisting of: $NH_2$, NHC(O)Ph, NHC(O)$CH_3$, NH($C_1$-$C_6$-alkyl), and N=CHN($C_1$-$C_6$-alkyl)$_2$;

$R^{21}$ is selected from the group consisting of: $NH_2$, NHC(O)CH($CH_3$)$_2$, NHC(O)N(Ph)$_2$, and N=CHN($C_1$-$C_6$-alkyl)$_2$;

$R^{22}$ is selected from the group consisting of: $NH_2$, NHC(O)Ph, NHC(O)$CH_3$, and N=CHN($C_1$-$C_6$-alkyl)$_2$;

$R^{23}$ is selected from the group consisting of: H, phenyl, 4-chlorophenyl, (4-nitrophenyl)ethyl, and 2-cyanoethyl;

Y is H, OH, $OCH_3$, —OSi(t-Bu)Me$_2$, —OCH$_2$OSi(i-Pr)$_3$, or —OCH(OCH$_2$CH$_2$OAC)$_2$; and W is H or —OP(OCH$_2$CH$_2$CN)N(i-Pr)$_2$.

18. The compound of claim 1 that is shown in formula IV below
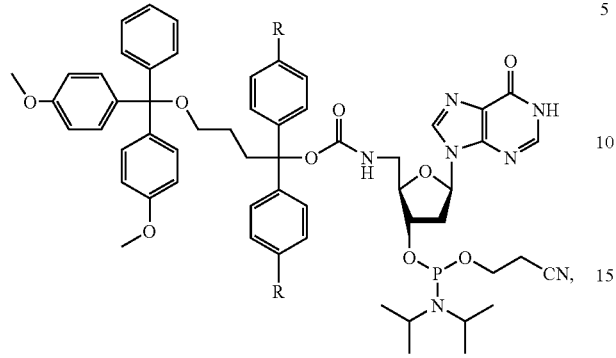
wherein R is H or Cl.
19. The compound of claim 1, wherein the compound is selected from the group consisting of:
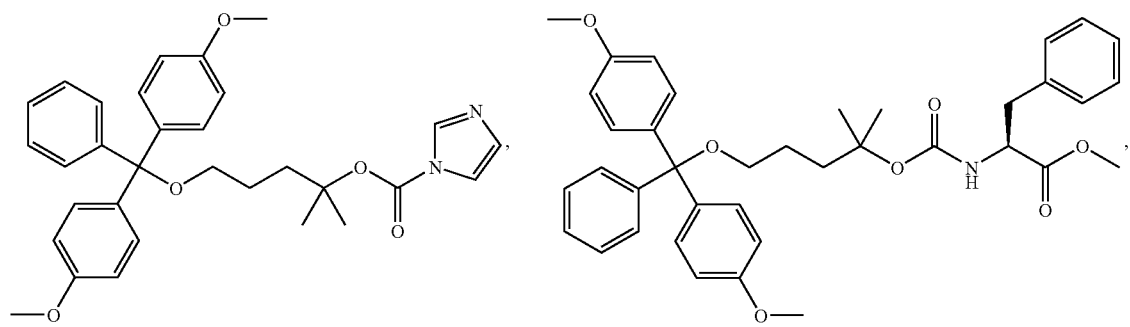
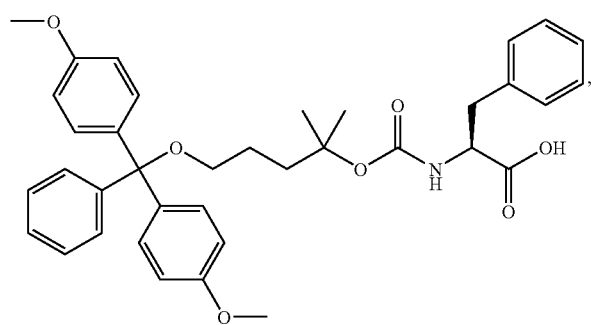
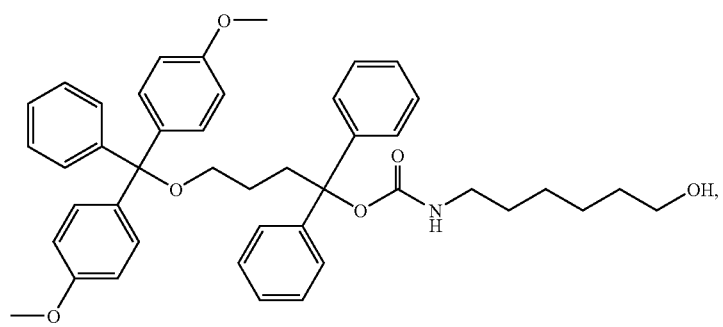

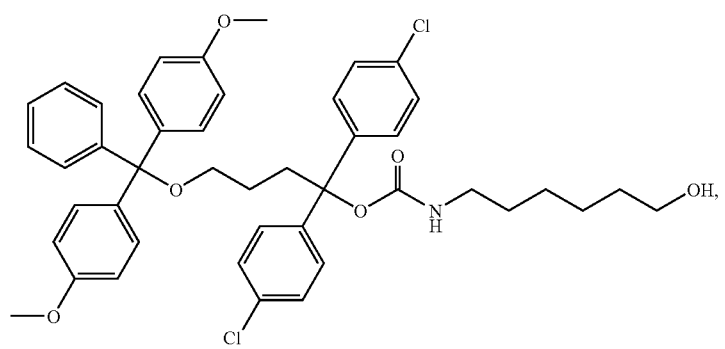
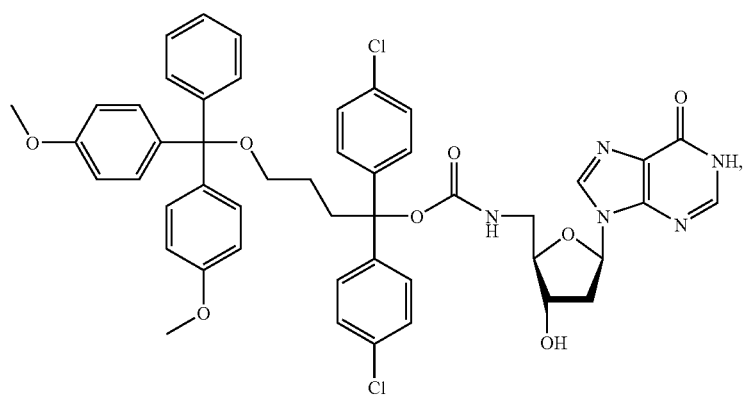
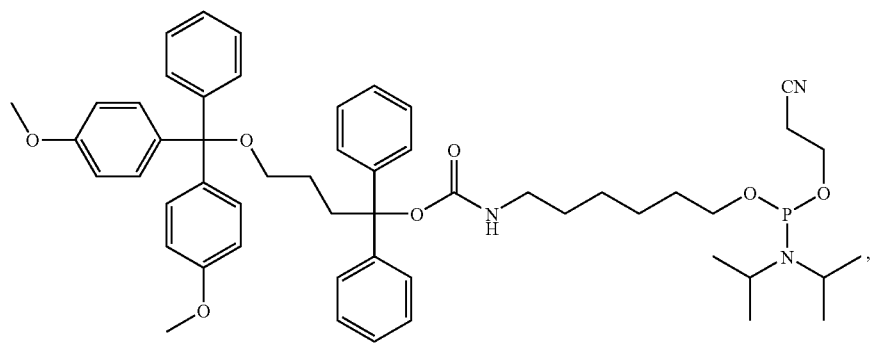
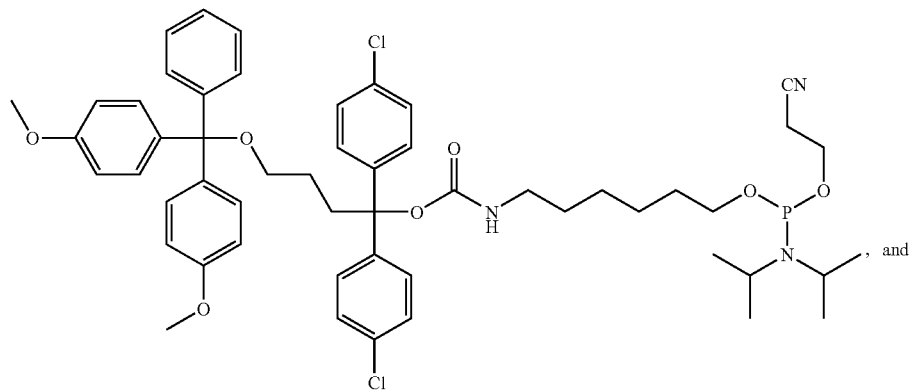

-continued

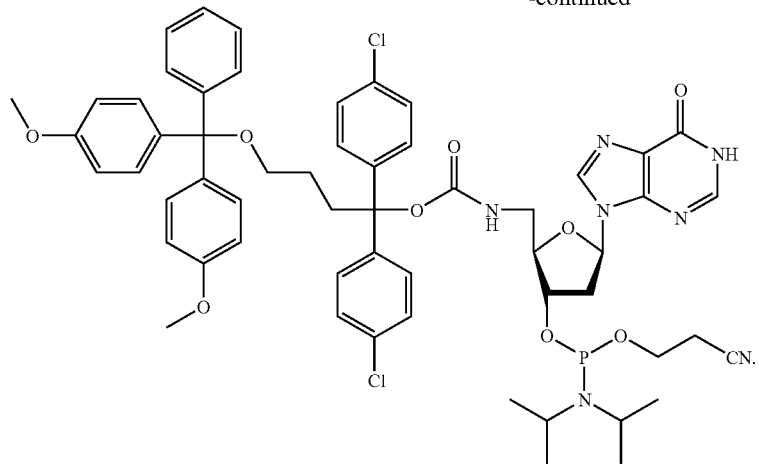

20. A compound of formula of the following formula:

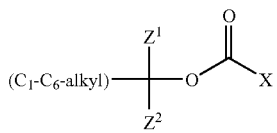

wherein
$Z^1$ and $Z^2$ are each independently aryl; and
X is selected from the group consisting of an acyl-leaving group, a $C_1$-$C_6$-alkyl ester of an amino acid, an active ester of an amino acid, an amino acid, an amino alcohol, an amino ether, an amino alcohol-O-phosphoramidite, an amino-nucleoside, an amino-nucleoside-O-phosphoramidite, and a diamine;
or a salt thereof.

* * * * *

UNITED STATES PATENT AND TRADEMARK OFFICE
CERTIFICATE OF CORRECTION

| | | |
|---|---|---|
| PATENT NO. | : 7,960,526 B2 | Page 1 of 1 |
| APPLICATION NO. | : 12/414288 | |
| DATED | : June 14, 2011 | |
| INVENTOR(S) | : John C. Hodges et al. | |

It is certified that error appears in the above-identified patent and that said Letters Patent is hereby corrected as shown below:

In the Claims

In column 40, claim 17, line 66, before "and" replace "OAC)$_2$;" with --OAc)$_2$;--.

Signed and Sealed this
Twenty-ninth Day of November, 2011

David J. Kappos
*Director of the United States Patent and Trademark Office*